United States Patent
Suzuki et al.

(10) Patent No.: US 9,120,085 B2
(45) Date of Patent: Sep. 1, 2015

(54) SILICA-BASED MATERIAL AND PROCESS FOR PRODUCING THE SAME, NOBLE METAL SUPPORTED MATERIAL AND PROCESS FOR PRODUCING CARBOXYLIC ACIDS BY USING THE SAME AS CATALYST

(75) Inventors: Ken Suzuki, Tokyo (JP); Tatsuo Yamaguchi, Tokyo (JP); Chihiro Iitsuka, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 227 days.

(21) Appl. No.: 13/820,892

(22) PCT Filed: Sep. 16, 2010

(86) PCT No.: PCT/JP2010/066084
§ 371 (c)(1),
(2), (4) Date: Mar. 5, 2013

(87) PCT Pub. No.: WO2012/035637
PCT Pub. Date: Mar. 22, 2012

(65) Prior Publication Data
US 2013/0172599 A1    Jul. 4, 2013

(51) Int. Cl.
| | |
|---|---|
| *B01J 21/04* | (2006.01) |
| *B01J 23/755* | (2006.01) |
| *B01J 21/08* | (2006.01) |
| *B01J 21/12* | (2006.01) |
| *B01J 35/10* | (2006.01) |
| *B01J 37/00* | (2006.01) |
| *B01J 37/03* | (2006.01) |
| *B82Y 30/00* | (2011.01) |
| *C01B 33/113* | (2006.01) |
| *C01B 33/18* | (2006.01) |
| *C07C 67/39* | (2006.01) |
| *C07C 51/25* | (2006.01) |
| *B01J 23/06* | (2006.01) |
| *B01J 23/66* | (2006.01) |
| *B01J 23/78* | (2006.01) |
| *B01J 23/83* | (2006.01) |
| *B01J 23/89* | (2006.01) |
| *C07C 51/235* | (2006.01) |
| *C07C 67/40* | (2006.01) |
| *B01J 37/10* | (2006.01) |
| *B01J 37/18* | (2006.01) |
| *B01J 23/889* | (2006.01) |
| *B01J 35/00* | (2006.01) |
| *B01J 37/02* | (2006.01) |

(52) U.S. Cl.
CPC ........... *B01J 23/755* (2013.01); *B01J 21/08* (2013.01); *B01J 21/12* (2013.01); *B01J 23/06* (2013.01); *B01J 23/66* (2013.01); *B01J 23/78* (2013.01); *B01J 23/83* (2013.01); *B01J 23/8896* (2013.01); *B01J 23/892* (2013.01); *B01J 23/8946* (2013.01); *B01J 23/8986* (2013.01); *B01J 35/006* (2013.01); *B01J 35/1019* (2013.01); *B01J 35/1038* (2013.01); *B01J 35/1061* (2013.01); *B01J 37/0045* (2013.01); *B01J 37/0201* (2013.01); *B01J 37/038* (2013.01); *B01J 37/10* (2013.01); *B01J 37/18* (2013.01); *B82Y 30/00* (2013.01); *C01B 33/113* (2013.01); *C01B 33/18* (2013.01); *C07C 51/235* (2013.01); *C07C 51/252* (2013.01); *C07C 67/39* (2013.01); *C07C 67/40* (2013.01); *B01J 23/894* (2013.01); *C01P 2004/64* (2013.01); *C01P 2006/12* (2013.01); *C01P 2006/14* (2013.01)

(58) Field of Classification Search
CPC ............................ B01J 20/3204; B01J 20/103
USPC ............................................. 502/439; 560/208
See application file for complete search history.

(56) References Cited

U.S. PATENT DOCUMENTS

| | | |
|---|---|---|
| 2004/0238410 A1 | 12/2004 | Inoue et al. |
| 2006/0014980 A1 | 1/2006 | Kawato et al. |
| 2007/0021629 A1 | 1/2007 | Stevenson et al. |
| 2009/0221849 A1 | 9/2009 | Begli et al. |

(Continued)

FOREIGN PATENT DOCUMENTS

| | | |
|---|---|---|
| EP | 2177267 A1 | 4/2010 |
| EP | 2210664 A1 | 7/2010 |
| JP | 60-96522 A | 5/1985 |

(Continued)

OTHER PUBLICATIONS

Office Action issued Jul. 30, 2013, in Japanese Patent Application No. 2009-068421.

(Continued)

*Primary Examiner* — Porfirio Nazario Gonzalez
*Assistant Examiner* — Kofi Adzamli
(74) *Attorney, Agent, or Firm* — Birch, Stewart, Kolasch & Birch, LLP

(57) ABSTRACT

A silica-based material comprising:
  silicon;
  aluminum;
  at least one fourth period element selected from the group consisting of iron, cobalt, nickel and zinc; and
  at least one basic element selected from the group consisting of alkali metal elements, alkali earth metal elements and rare earth elements,
  wherein the silica-based material comprises 42 to 90 mol % of the silicon, 3 to 38 mol % of the aluminum, 0.5 to 20 mol % of the fourth period element and 2 to 38 mol % of the basic element, based on a total mole of the silicon, the aluminum, the fourth period element and the basic element.

5 Claims, No Drawings

(56) References Cited

U.S. PATENT DOCUMENTS

| | | | |
|---|---|---|---|
| 2010/0249448 A1* | 9/2010 | Suzuki et al. | 560/208 |
| 2011/0184206 A1* | 7/2011 | Suzuki et al. | 560/103 |

FOREIGN PATENT DOCUMENTS

| | | |
|---|---|---|
| JP | 6-256011 A | 9/1994 |
| JP | 8-215544 A | 8/1996 |
| JP | 9-52044 A | 2/1997 |
| JP | 2001-17222 A | 6/2001 |
| JP | 2003-192632 A | 7/2003 |
| JP | 2004-141828 A | 5/2004 |
| JP | 2004-209406 A | 7/2004 |
| JP | 2007-245068 A | 9/2007 |
| JP | 2009-502491 A | 1/2009 |
| JP | 2010-221081 A | 10/2010 |
| JP | 2010-221082 A | 10/2010 |
| JP | 2010-221083 A | 10/2010 |
| JP | 2010-222151 A | 10/2010 |
| JP | 5335505 B2 | 8/2013 |
| JP | 5336234 B2 | 8/2013 |
| JP | 5336235 B2 | 8/2013 |
| KR | 10-2010-0019569 A | 2/2010 |
| WO | WO 2009/022544 A1 | 2/2009 |
| WO | WO 2009022544 A1 * | 2/2009 |
| WO | WO 2009/054462 A1 | 4/2009 |
| WO | WO 2009054462 A1 * | 4/2009 |

OTHER PUBLICATIONS

English translation of International Preliminary Report on Patentability and Written Opinion issued Apr. 9, 2013, in PCT International Application No. PCT/JP2010/066084.

International Search Report issued Dec. 21, 2010, in PCT International Application No. PCT/JP2010/066084.

Office Action issued on Apr. 22, 2014 for Korean Patent Application No. 10-2013-7003812.

Office Action issued Dec. 6, 2013, in Japanese Patent Application No. 2009-257201.

European Search Report dated Feb. 2, 2015, for European Application No. 10857271.0.

* cited by examiner

SILICA-BASED MATERIAL AND PROCESS FOR PRODUCING THE SAME, NOBLE METAL SUPPORTED MATERIAL AND PROCESS FOR PRODUCING CARBOXYLIC ACIDS BY USING THE SAME AS CATALYST

TECHNICAL FIELD

The present invention relates to a silica-based material and a process for producing the same, and a noble metal-supported material and a process for producing carboxylic acids by using the same as a catalyst.

BACKGROUND ART

Silica-based materials have been put to a variety of uses as materials with their characteristics applied. Examples of the uses are a filler for liquid chromatography, a base for cosmetics, a catalyst, a catalyst support, a flow adjuster and a diluent. As one of means for attaining physical properties such as a high specific surface area meeting requirements for these uses, a silica-based material may be modified to be porous, but in this case, the mechanical strength of the silica-based material is reduced. On the other hand, when a precursor of a silica-based material is calcined at a high temperature for increasing the mechanical strength of the silica-based material, its specific surface area is reduced. In this manner, it is difficult to obtain a silica-based material satisfying conflicting physical properties, i.e., high mechanical strength and a high specific surface area, and a silica-based material meeting both of these requirements has not been obtained yet.

Quartz, that is, one of silica-based materials, is known to be hard and have high mechanical strength. Although quartz is generally superior in mechanical strength, however, it has a small specific surface area (of 1 $m^2/g$ or less), and hence, it may not be used for a use requiring a high specific surface area. Although a silica-based material may be synthesized to attain a high specific surface area so as to be used as a catalyst support in some cases, the mechanical strength is sacrificed in such cases, and no silica-based material shows both a high specific surface area and high mechanical strength in these cases.

Patent Literature 1 describes, as a catalyst support for use in producing carboxylic acid ester, silica-alumina-magnesia including 5 to 40 wt % of aluminum in terms of $Al_2O_3$, 3 to 30 wt % of magnesium in terms of MgO and 50 to 92 wt % of silicon in terms of $SiO_2$.

CITATION LIST

Patent Literature

Patent Literature 1: Japanese Patent Laid-Open No. 9-52044

SUMMARY OF INVENTION

Technical Problem

The silica-alumina-magnesia support described in Patent Literature 1 has characteristics of high mechanical strength and a high specific surface area as well as high water resistance as compared with silica and high acid resistance as compared with alumina. When the support is used as a catalyst support for use in producing carboxylic acid ester, however, although satisfactory mechanical strength may be attained under general use conditions, there may arise a problem of break or crack in a reaction under conditions of vigorous mixture or the like due to friction or the like caused among particles or between particles and stirring blades, for example, in a suspension reaction performed under severe conditions.

Moreover, the present inventors have found through examination that, in the case where a reaction is conducted for a long period of time by using a catalyst including the support described in Patent Literature 1, increase of a pore size and structural change of a catalyst particle derived from particle growth are caused although gradually. The increase of the pore size seems to be caused for the following reason: Since catalyst particles are locally exposed to an acid and a base repeatedly through by-production of an acid component and addition of an alkali component peculiar to the reaction, part of silicon and aluminum included in the silica-alumina-magnesia support is dissolved and precipitated, and hence, a silica alumina crosslinked structure is rearranged, which probably increases the pore size. It has been also found that the particle growth proceeds through sintering of a supported noble metal simultaneously with the increase of the pore size, resulting in lowering catalytic activity.

The present invention has been achieved in consideration of the aforementioned circumstances, and an object of the invention is to provide a silica-based material having high mechanical strength and a high specific surface area and excellent in resistance to acids and bases, a process for producing the same and a noble metal-supported material including the silica-based material.

Solution to Problem

From the viewpoint of improving chemical stability and mechanical strength of a silica gel, the present inventors have paid attention to a specific structure of a silica chain (—Si—O—) constructing a silica gel and have earnestly studied correlation between the structure and the physical properties. As a result, it has been unexpectedly found that a silica-based material made of a composite oxide comprising silicon; aluminum; at least one element selected from the group consisting of iron, cobalt, nickel and zinc; and at least one basic element selected from the group consisting of alkali metal elements, alkali earth metal elements and rare earth elements is excellent in resistance to acids and bases and may solve the aforementioned problems by overcoming the above-described various disadvantages of the conventional silica-based material, and thus, the present invention has been accomplished.

Specifically, the present invention provides the following:

[1]
A silica-based material comprising:
silicon;
aluminum;
at least one fourth period element selected from the group consisting of iron, cobalt, nickel and zinc; and
at least one basic element selected from the group consisting of alkali metal elements, alkali earth metal elements and rare earth elements,
wherein the silica-based material comprises 42 to 90 mol % of the silicon, 3 to 38 mol % of the aluminum, 0.5 to 20 mol % of the fourth period element and 2 to 38 mol % of the basic element, based on a total mole of the silicon, the aluminum, the fourth period element and the basic element.

[2]
The silica-based material according to [1], in which a composition ratio of the fourth period element to the aluminum is 0.02 to 2.0 on a mole basis.

[3]

The silica-based material according to [1] or [2], in which a composition ratio of the fourth period element to the basic element is 0.02 to 2.0 on a mole basis.

[4]

The silica-based material according to any one of [1] to [3], in which the fourth period element is nickel, the basic element is magnesium, and the silica-based material comprises 42 to 90 mol % of the silicon, 3 to 38 mol % of the aluminum, 0.5 to 20 mol % of the nickel and 2 to 38 mol % of the magnesium, based on a total mole of the silicon, the aluminum, the nickel and the magnesium.

[5]

A process for producing a silica-based material comprising silicon, aluminum, at least one fourth period element selected from the group consisting of iron, cobalt, nickel and zinc and at least one basic element selected from the group consisting of alkali metal elements, alkali earth metal elements and rare earth elements, and comprising 42 to 90 mol % of the silicon, 3 to 38 mol % of the aluminum, 0.5 to 20 mol % of the fourth period element and 2 to 38 mol % of the basic element, based on a total mole of the silicon, the aluminum, the fourth period element and the basic element, the process comprising the steps of:

obtaining a composition including silica, an aluminum compound, at least one compound of fourth period elements selected from the group consisting of iron, cobalt, nickel and zinc, and at least one compound of basic elements selected from the group consisting of alkali metal elements, alkali earth metal elements and rare earth elements; and obtaining a solid material by calcining the composition or a dried substance of the composition.

[6]

The process for producing the silica-based material according to [5], further comprising a step of subjecting the solid material to a hydrothermal treatment.

[7]

A process for producing a silica-based material comprising silicon, aluminum, at least one fourth period element selected from the group consisting of iron, cobalt, nickel and zinc and at least one basic element selected from the group consisting of alkali metal elements, alkali earth metal elements and rare earth elements, and comprising 42 to 90 mol % of the silicon, 3 to 38 mol % of the aluminum, 0.5 to 20 mol % of the fourth period element and 2 to 38 mol % of the basic element, based on a total mole of the silicon, the aluminum, the fourth period element and the basic element, the process comprising the steps of:

obtaining a solid material by calcining a composition including silica, an aluminum compound, and at least one compound of basic elements selected from the group consisting of alkali metal elements, alkali earth metal elements and rare earth elements, or a dried substance of the composition;

neutralizing a mixture of the solid material and an acidic aqueous solution of a soluble metal salt including at least one fourth period element selected from the group consisting of iron, cobalt, nickel and zinc, to cause a component including the fourth period element to deposit on the solid material;

subjecting the solid material on which the fourth period element has been deposited to a hydrothermal treatment; and subjecting the solid material having been subjected to the hydrothermal treatment to a heat treatment.

[8]

A noble metal-supported material comprising:

a silica-based material according to any one of [1] to [4] described above; and at least one noble metal component supported on the silica-based material and selected from the group consisting of ruthenium, rhodium, palladium, silver, rhenium, osmium, iridium, platinum and gold.

[9]

The noble metal-supported material according to [8], in which the noble metal component has an average particle size of 2 to 10 nm.

[10]

A process for producing a carboxylic acid ester comprising reacting aldehyde with alcohol in the presence of the noble metal-supported material according to [8] or [9] described above and oxygen.

[11]

The process for producing the carboxylic acid ester according to [10], in which the aldehyde is at least one selected from the group consisting of acrolein, methacrolein and a mixture of the acrolein and the methacrolein.

[12]

The process for producing the carboxylic acid ester according to [10], in which the aldehyde is at least one selected from the group consisting of acrolein, methacrolein and a mixture of the acrolein and the methacrolein, and the alcohol is methanol.

[13]

A process for producing a carboxylic acid comprising oxidizing aldehyde in the presence of the noble metal-supported material according to [8] or [9] described above to produce carboxylic acid.

[14]

The process for producing the carboxylic acid according to [13], in which the aldehyde is at least one selected from the group consisting of acrolein, methacrolein and a mixture of the acrolein and the methacrolein.

Advantageous Effects of Invention

According to the present invention, a silica-based material that has high mechanical strength and a high specific surface area and is excellent in resistance to acids and bases, and a noble metal-supported material including the silica-based material may be provided.

DESCRIPTION OF EMBODIMENT

An embodiment for practicing the present invention (hereinafter simply referred to as the "present embodiment") will now be described in detail. It is noted that the present invention is not limited to the following embodiment but may be variously modified within the scope of the invention.

A silica-based material of the present embodiment comprises:

silicon;

aluminum;

at least one fourth period element selected from the group consisting of iron, cobalt, nickel and zinc; and at least one basic element selected from the group consisting of alkali metal elements, alkali earth metal elements and rare earth elements, wherein the silica-based material comprises 42 to 90 mol % of the silicon, 3 to 38 mol % of the aluminum, 0.5 to 20 mol % of the fourth period element and 2 to 38 mol % of the basic element, based on a total mole of the silicon, the aluminum, the fourth period element and the basic element.

A silica-based material of the present embodiment is made of a composite oxide comprising silicon, aluminum, at least one fourth period element selected from the group consisting of iron (Fe), cobalt (Co), nickel (Ni) and zinc (Zn), and at least one basic element selected from the group consisting of alkali metal elements, alkali earth metal elements and rare earth elements, and is what is called a silica composite material.

Characteristics of the silica-based material of the present embodiment will now be described. In the present embodiment, the resistance to acids and bases and the mechanical strength of the silica-based material are largely improved probably for the following reason:

In the silica-based material of the present embodiment, since aluminum (Al) coexists in silica having an uncrosslinked silica chain (Si—O) like a silica gel, a crosslinked structure of the Si—O chain through Al, such as a Si—O—Al—O—Si bond, (hereinafter sometimes referred to as the "silica alumina crosslinked structure") seems to be newly formed so that the crosslinked structure through Al may be formed without losing stability against an acidic substance peculiar to the Si—O chain. As a result, it seems that not only the Si—O bond is enhanced but also stability against hydrolysis (hereinafter sometimes simply referred to as the "water resistance") is remarkably improved. Furthermore, when the silica alumina crosslinked structure is formed, an amount of Si—O uncrosslinked chain is probably reduced as compared with that in single silica, which may also improve mechanical strength. In other words, it is presumed that there is correlation between the amount of silica alumina crosslinked structure to be formed and improvement in the mechanical strength and the water resistance of the resultant silica-based material.

As the silica alumina crosslinked structure is produced, charge becomes unstable due to a difference in valence between Si (with a valence of 4) and Al (with a valence of 3). Therefore, in the silica-based material of the present embodiment, in addition to the silicon and the aluminum, at least one basic element selected from the group consisting of alkali metal elements, alkali earth metal elements and rare earth elements coexists. Thus, the charge is stabilized through compensation neutralization caused by the basic element with a valence of 1 to 3. Furthermore, it is presumed that the stability of the structure is further improved because it is better balanced in terms of charge by employing a three-component system. As one of grounds for the presumption, silica-alumina-magnesia is substantially neutral while silica-alumina is acid.

The silica-based material of the present embodiment further includes, in addition to the three component elements, at least one fourth period element selected from the group consisting of iron, cobalt, nickel and zinc, and therefore, the resistance to acids and bases is improved as compared with one not including such a fourth period element. Accordingly, even under a pH swing condition where the material is repeatedly exposed to an acid and a base, high structural stability may be attained, and increase of a pore size and decrease of a specific surface area may be suppressed.

According to examination made by the present inventors, it has been revealed that when silica-alumina or silica-alumina-magnesia is repeatedly exposed to an acid and a base, the structure of such a silica-based material is changed although gradually. This phenomenon seems to be caused as follows: Since such a silica-based material is locally exposed to an acid and a base repeatedly, part of silicon and aluminum included in the silica-based material is dissolved and precipitated, and hence, the silica alumina crosslinked structure is rearranged, so as to increase the pore size of the silica-based material, which causes the structural change. In addition, in a metal-supported material including a noble metal-supported by the aforementioned silica-based material, it has been found that sintering is caused in the supported noble metal as the pore size is increased through the pH swing, which reduces the specific surface area of the noble metal so as to lower the catalytic activity.

On the other hand, in the silica-based material of the present embodiment, it seems that the fourth period element reacts with aluminum and/or a basic element included in the silica-based material so as to produce a composite oxide including the fourth period element. The production of such a compound seems to affect the stability of the silica alumina crosslinked structure, resulting in improving the resistance to acids and bases of the silica-based material and largely improving the structural change.

The term "composite oxide" herein means an oxide including two or more metals. Specifically, the "composite oxide" includes a double oxide (such as a perovskite oxide or a spinel oxide of nickel) that is an oxide formed as a compound by two or more metal oxides and includes no ions of oxo acid as a structural unit thereof. The term has, however, a larger concept than the double oxide and implicates all oxides in which two or more metals are compounded. An oxide formed as a solid solution by two or more metal oxides also belongs to the category of the "composite oxide."

For example, nickel is selected as the fourth period element and magnesium is selected as the basic element, so as to obtain a silica-based material made of a composite oxide comprising silicon-aluminum-nickel-magnesium, and when a chemical state of the nickel in this silica-based material is analyzed through high-resolution X-ray fluorescence (HRXRF) spectroscopy, the nickel included in the silica-based material of the present embodiment is not present as a single compound of nickel oxide. The nickel is present as a composite oxide including nickel, such as an oxide compound or a solid solution of nickel produced through bond of nickel oxide, alumina and/or magnesia, or a mixture of the compound and the solid solution.

The high-resolution X-ray fluorescence (HRXRF) spectroscopy has extremely high energy resolution and may analyze a chemical state of an element on the basis of an energy position (chemical shift) or a shape of an obtained spectrum. In particular, in a Kα spectrum of a 3d transition metal element, the chemical shift or the spectral shape is changed in accordance with change of a valence or an electron state, and thus, the chemical state of the element may be analyzed in detail. The silica-based material of the present embodiment is different in a NiKα spectrum as compared with that of nickel oxide, and therefore, a chemical state of nickel different from that of a single compound of nickel oxide is found.

It is presumed that the nickel is present, in the silica-based material of the present embodiment, for example, as nickel aluminate ($NiAl_2O_4$), that is, a spinel compound of nickel oxide and alumina, or a solid solution of nickel oxide and magnesia (NiO.MgO). As for each of the fourth period elements other than nickel, it seems that an oxide thereof forms a spinel compound with alumina or a solid solution with a basic metal oxide, so as to stabilize the silica alumina crosslinked structure, resulting in attaining high chemical stability.

The silica-based material of the present embodiment is not particularly limited in its specific surface area, but when it is used as a support, the specific surface area is preferably 20 to 500 $m^2/g$, more preferably 50 to 400 $m^2/g$ and further more preferably 50 to 350 m²/g. The specific surface area of the silica-based material is preferably 20 m²/g or more from the viewpoint of easiness in supporting a supported component such as a noble metal when the silica-based material is used as a support and from the viewpoint of catalytic activity when the metal-supported material is used as a catalyst. Furthermore, the specific surface area of the silica-based material is preferably 500 m²/g or less from the viewpoint of the mechanical strength and the water resistance.

When the silica-based material is used as a catalyst support, the pore size is preferably 3 to 50 nm, more preferably 3 to 30 nm and further more preferably 3 to 10 nm. When the catalyst is used in a liquid phase reaction, the pore size is preferably 3 nm or more from the viewpoint of retaining high reaction activity without excessively increasing diffusion resistance within pores so as not to make a diffusion process of a reaction matrix rate-determining. On the other hand, the pore size is preferably 50 nm or less from the viewpoint that the catalyst is difficult to break and a supported component such as a noble metal is difficult to peel off.

The silica-based material has a pore volume of preferably 0.1 to 1.0 mL/g and more preferably 0.1 to 0.5 mL/g from the viewpoint of strength and supporting characteristics. The pores formed in the silica-based material are necessary for supporting a component to be supported. The silica-based material of the present embodiment preferably has a specific surface area, a pore size and a pore volume within the aforementioned ranges from the viewpoint of the mechanical strength and the water resistance. The specific surface area, the pore size and the pore volume of the silica-based material are measured in accordance with methods described later.

The silica-based material made of the composite oxide comprising the silicon, the aluminum, the fourth period element and the basic element includes 42 to 90 mol % of the silicon, 3 to 38 mol % of the aluminum, 0.5 to 20 mol % of the fourth period element and 2 to 38 mol % of the basic element, based on the total mole of the silicon, the aluminum, the fourth period element and the basic element. When the amounts of the silicon, the aluminum, the fourth period element and the basic elements fall within the aforementioned ranges, the silicon, the aluminum, the fourth period element, the basic element and oxygen atoms together form a specific stable bonding structure, and in addition, the bonding structure may be easily formed in a homogeneously dispersed state within the silica-based material. The silica-based material preferably includes 70 to 90 mol % of the silicon, 5 to 30 mol % of the aluminum, 0.75 to 15 mol % of the fourth period element and 2 to 30 mol % of the basic element, and more preferably includes 75 to 90 mol % of the silicon, 5 to 15 mol % of the aluminum, 1 to 10 mol % of the fourth period element and 2 to 15 mol % of the basic element. Particularly, when the composition ratio of the fourth period element is 0.75 mol % or more and the respective components are dispersed homogeneously in the whole material, minimum portions within the structure lack the fourth period element, and hence, a silica-based material capable of showing resistance even when the material is repeatedly exposed to an acid and/or a base (namely, having high resistance to acids and bases) may be obtained. From the viewpoint of obtaining a silica-based material having high mechanical strength and a high specific surface area, the amounts of the fourth period element and the basic element are preferably 10 mol % or less and 30 mol % or less, respectively. The composition ratios of the silicon and the aluminum are set in suitable ranges from the viewpoint of the resistance to acids and bases and the water resistance of the silica-based material. A composition ratio of the silicon to the aluminum (silicon/aluminum) is preferably 2 to 4. When the ratio (silicon/aluminum) is below this range, the resistance to acids and bases is liable to be lowered. When the ratio (silicon/aluminum) is beyond the range, the water resistance is liable to be lowered.

Examples of the alkali metal elements of the basic element are lithium (Li), sodium (Na), potassium (K), rubidium (Rb) and cesium (Cs), examples of the alkali earth metal elements are beryllium (Be), magnesium (Mg), calcium (Ca), strontium (Sr) and barium (Ba), and examples of the rare earth elements are lanthanum (La), cerium (Ce) and praseodymium (Pr).

In the present embodiment, there is a suitable range of a composition ratio between the fourth period element and the aluminum or the basic element. A composition ratio (the fourth period element/aluminum) of the fourth period element to the aluminum is preferably 0.02 to 2.0, more preferably 0.05 to 1.75 and further more preferably 0.1 to 1.2 on a mole basis. Furthermore, a composition ratio (the fourth period element/the basic element) of the fourth period element to the basic element is preferably 0.02 to 2.0, more preferably 0.05 to 1.75 and further more preferably 0.1 to 1.2 on a mole basis. When the composition ratios of the fourth period element to the aluminum or the basic element fall within the aforementioned ranges, an effect to improve elution of the aluminum and the structural change of the silica-based material is liable to be increased. This is probably because the fourth period element, the aluminum and the basic element together form a specific composite oxide so as to attain a stable bonding structure when the composition ratios fall in these ranges. In other words, when the proportion of the fourth period element to the basic element or the aluminum is too low in the silica-based material, although a preferable structure is locally formed, it may not be necessarily formed over the whole silica-based material in a sufficient existing density. On the contrary, when the aforementioned composition ratios, particularly the ratio (the fourth period element/the aluminum) of 0.05 to 1.75 and the ratio (the fourth period element/the basic element) of 0.05 to 1.75, are satisfied, it seems that the preferable structure may be present to an extent to make a contribution to the stabilization of the whole material.

In the case where the fourth period element is nickel and the basic element is magnesium, a silica-based material made of a composite oxide comprising silicon, aluminum, nickel and magnesium includes, from the viewpoint of the resistance to acids and bases, the mechanical strength and the water resistance, preferably 42 to 90 mol % of silicon, 3 to 38 mol % of aluminum, 0.5 to 20 mol % of nickel and 2 to 38 mol % of magnesium, based on the total mole of the silicon, the aluminum, the nickel and the magnesium. More preferably, it includes 70 to 90 mol % of silicon, 5 to 30 mol % of aluminum, 0.75 to 15 mol % of nickel and 2 to 30 mol % of magnesium, and further more preferably, it includes 75 to 90 mol % of silicon, 5 to 15 mol % of aluminum, 1 to 10 mol % of nickel and 2 to 15 mol % of magnesium. When the element compositions of silicon, aluminum, nickel and magnesium fall in the above-described ranges, the silicon, the aluminum, the nickel and the magnesium easily form a specific stable bonding structure. In particular, when the composition ratios fall within the more preferable range, even assuming that the stable bonding structure is homogeneously dispersed in the silica-based material, it is expected to be formed in a sufficient existing density for making contribution to the stabilization of the whole silica-based material. As a result, the silica-based material is liable to show resistance to acids and bases and mechanical strength sufficiently high for withstanding repeated uses.

A solid form of the silica-based material of the present embodiment is not particularly limited as far as it may attain prescribed physical properties.

A dispersion state of the fourth period element in the silica-based material of the present embodiment is not particularly limited, but from the viewpoint of stabilizing the structure of the whole silica-based material, it is preferably uniformly dispersed in the whole material. Specifically, the fourth period element is preferably present in substantially the same concentration in all observation portions in a cross-section of the silica-based material observed by electron probe microanalysis (EPMA). In such a dispersion state, the specific stable bonding structure formed by the silicon, the aluminum, the fourth period element and the basic element is present to the extent to make contribution to the stabilization of the whole material, and the resistance to acids and bases is liable to be retained even through long-term repeated use. At this point, the term "substantially the same concentration" means a state where a distribution range of measured values is within 10%.

A substantial thickness or particle size of the silica-based material may be various amplitudes in the order of μm to cm, and a shape thereof is also not particularly limited. Specific examples of the shape of the silica-based material are a sphere, an ellipse, a cylinder, a tablet, a hollow cylinder, a plate, a bar, a sheet and a honeycomb. When it is used as a catalyst or a catalyst support, the shape of the silica-based material of the present embodiment may be appropriately changed in accordance with a reaction system to be employed. When the silica-based material is used, for example, in a fixed bed reaction, it is preferably in the shape of a hollow cylinder or a honeycomb causing small pressure loss, and when it is used under a liquid phase slurry suspension condition, a spherical shape is generally preferably employed. In particular, when the silica-based material is used as a support for a catalyst used in a fluid bed reaction, it is preferably in the shape of spherical particles having an average particle size of preferably 1 to 200 more preferably 10 to 200 μm, and further more preferably 30 to 150 μm. When the silica-based material is thus used in the shape of particles, the excellent effects of the present invention may be more effectively and definitely brought. The average particle size of the silica-based material is measured in accordance with a method described later.

The silica-based material made of a composite oxide comprising silicon, aluminum, the fourth period element and the basic element has higher water resistance than silica and higher acid resistance than alumina. Furthermore, the silica-based material has excellent physical properties such as higher mechanical strength than silica. In addition, the silica-based material is extremely highly chemically stable as compared with silica-alumina or silica-alumina-magnesia, and it is possible to suppress the structural change such as the increase of the pore size and the decrease of the specific surface area otherwise caused by the dissolution and elution of part of silicon and aluminum, for example, under the pH swing condition in which it is exposed to an acid and a base repeatedly.

A process for producing the silica-based material of the present embodiment having the aforementioned composition will now be described.

The process for producing a silica-based material made of a composite oxide comprising silicon, aluminum, the fourth period element and the basic element is not particularly limited, but includes a step of obtaining a composition including silica, an aluminum compound, a compound of a fourth period element and a compound of a basic element by, for example, any of the following methods (1) to (6); a step of obtaining a dried substance by drying the composition if necessary; and a step of calcining the dried substance or the composition under conditions described later.

(1) A commercially available silica-alumina composition, a compound of a fourth period element and a compound of a basic element are reacted.

(2) A silica-alumina gel is preliminarily formed, and a compound of a fourth period element and a compound of a basic element are added to the gel to be reacted.

(3) A silica sol, an aluminum compound, a compound of a fourth period element and a compound of a basic element are reacted.

(4) A silica sol, a water-insoluble aluminum compound, a water-insoluble compound of a fourth period element and a water-insoluble compound of a basic element are reacted.

(5) A silica gel and an aqueous solution of a water-soluble aluminum compound, a water-soluble compound of a fourth period element and a water-soluble compound of a basic element are reacted.

(6) A silica gel, an aluminum compound, a compound of a fourth period element and a compound of a basic element are reacted in a solid phase.

Now, preparation processes for the silica-based material by employing the methods (1) to (6) will be described in detail.

In employing the method (1), a compound including a fourth period element and a compound including a basic element are mixed with a commercially available silica-alumina composition, so as to give slurry. The slurry is dried and then calcined under conditions described later, and thus, a silica-based material may be prepared. As the compound including a fourth period element and the compound including a basic element, water-soluble compounds represented by chlorides, carbonates, nitrates and acetates are preferably used. However, water-insoluble compounds such as hydroxides and oxides may be used.

In employing the methods (2) to (6), as a silica source, for example, a silica sol, water glass or a silica gel may be used. The silica gel is not limited as far as it has an uncrosslinked Si site to be reacted with Al, and the length of a Si—O chain is not particularly limited. As the aluminum compound, water-soluble compounds represented by soda aluminate, aluminum chloride hexahydrate, aluminum perchlorate hexahydrate, aluminum sulfate, aluminum nitrate nonahydrate and aluminum diacetate are preferred. However, water-insoluble compounds such as aluminum hydroxide and aluminum oxide may be used, and any compound that may react with uncrosslinked Si in a silica sol or a silica gel may be used for the preparation of the silica-based material. Examples of the compounds including a fourth period element or a basic element are an oxide, a hydroxide, a chloride, a carbonate, a sulfate, a nitrate and an acetate of such an element.

In employing the method (2) using a silica-alumina gel, a silica hydrogel with pH 8 to 10.5 is preliminarily prepared by adding sulfuric acid to water glass, an $Al_2(SO_4)_3$ solution with pH 2 or less is added to the gel, and soda aluminate with pH 5 to 5.5 is further added thereto, whereby preparing a silica-alumina hydrogel. Subsequently, a water content included in the hydrogel is adjusted to 10 to 40% by spray drying or the like, and a compound of a fourth period element and a compound of a basic element are added thereto, so as to give a composition. Then, the composition is dried, and then calcined under conditions described later, and thus, a silica-based material may be obtained.

In employing the methods (3) and (4) using a silica sol as a starting material, an aluminum compound, a compound of a fourth period element and a compound of a basic element are mixed with the silica sol, so as to give a mixed sol, that is, a composition including the silica sol, the aluminum compound, the compound of the fourth period element and the compound of the basic element, and subsequently, the mixed sol is dried to obtain a gel, and the gel is calcined under conditions of a temperature, time and an atmosphere described later. Alternatively, an alkaline aqueous solution is added to the mixed sol, so as to coprecipitate silica, the aluminum compound, the compound of the fourth period element and the compound of the basic element, and the thus obtained coprecipitated substance is dried and then calcined under conditions described later. Furthermore, a silica-based material having a desired particle size may be obtained through a step in which the mixed sol is dried by using a spray dryer and pulverized or a gel obtained by drying the mixed sol is granulated.

In employing the method (4), the silica sol is reacted with a water-insoluble aluminum compound, a water-insoluble compound of a fourth period element and a water-insoluble compound of a basic element, and at this point, each of or a mixture of the aluminum compound, the compound of the fourth period element and the compound of the basic element may be preliminarily crushed into a prescribed particle size or may be preliminarily coarsely crushed. After mixing and reacting the silica sol with the water-insoluble aluminum compound, the water-insoluble compound of the fourth period element and the water-insoluble compound of the basic element, the resultant reactant is dried, and then calcined under conditions described later. Incidentally, without preliminarily crushing or preliminarily coarsely crushing the aluminum compound, the compound of the fourth period element and the compound of the basic element, the silica-alumina-fourth period element-basic element composition obtained after calcining may be crushed into a prescribed particle size.

In employing the method (5) using a silica gel as a starting material, the silica gel is reacted with a water-soluble aluminum compound, a water-soluble compound of a fourth period element and a water-soluble compound of a basic element, and at this point, the silica gel may be preliminarily crushed into a prescribed particle size or preliminarily coarsely crushed. In employing the method (5), after obtaining a slurry by mixing the silica gel with an aqueous solution of the water-soluble aluminum compound, an aqueous solution of the water-soluble compound of the fourth period element and an aqueous solution of the water-soluble compound of the basic element, the slurry is dried, and then calcined for 1 to 48 hours under conditions described later. Alternatively, without preliminarily crushing or preliminarily coarsely crushing the silica gel, the silica-alumina-fourth period element-basic element composition obtained after calcining may be crushed into a prescribed particle size.

In employing the method (6) also using a silica gel as a starting material, the silica gel, an aluminum compound, a compound of a fourth period element and a compound of a basic element are reacted with in a solid phase, whereby obtaining a composition as a reactant. In this case, Al is reacted with uncrosslinked Si in a solid phase state. The silica gel, the aluminum compound, the compound of the fourth period element and the compound of the basic element may be preliminarily crushed into a prescribed particle size, or may be preliminarily coarsely crushed. At this point, the respective compounds may be each singly crushed, or a mixture thereof may be crushed. The reactant obtained through the solid phase reaction is dried if necessary, and is then calcined. The calcining is preferably conducted under conditions of a temperature, time and an atmosphere described later. Without preliminarily crushing or preliminarily coarsely crushing the silica gel, the aluminum compound, the compound of the fourth period element and the compound of the basic element, the reactant obtained through the reaction may be crushed into a desired particle size As another preparation process for a composition including silica, an aluminum compound, a compound of a fourth period element and a compound of a basic element, a process in which a component of a basic element is adsorbed onto a silica-based material made of a composite oxide comprising silicon, aluminum and a fourth period element may be employed. In this case, for example, a method employing immersion for adding the silica-based material to a liquid of a compound of the basic element dissolved therein and drying the resultant material, or a method employing impregnation for impregnating the silica-based material with a compound of the basic element in an amount corresponding to a pore volume and drying the resultant silica-based material may be applied.

A method in which a component including a fourth period element is adsorbed onto a silica-based material made of a composite oxide comprising silicon, aluminum and a basic element may be employed. In this case, for example, a method employing immersion for adding the silica-based material to a liquid of a compound of a fourth period element dissolved therein and drying the resultant material, or a method employing impregnation for impregnating the silica-based material with a compound including a fourth period element in an amount corresponding to a pore volume and drying the resultant silica-based material may be applied. In employing the method in which a component including a basic element or a component including a fourth period element is subsequently adsorbed, however, it is necessary to pay attention to performing a drying process under relaxed conditions for highly dispersing the component including the basic element or the component including the fourth period element in the silica-based material.

To the slurry including the respective raw materials obtained as described above, an inorganic substance or an organic substance may be added for controlling properties of the slurry and finely adjusting characteristics such as a porous structure of a product and physical properties to be obtained. Specific examples of the inorganic substance are mineral acids such as nitric acid, chloric acid and sulfuric acid; metal salts including alkali metals such as Li, Na, K, Rb and Cs, and alkali earth metals such as Mg, Ca, Sr and Ba; water-soluble compounds such as ammonia and ammonium nitrate; and clay minerals dispersed in water to produce suspensions. Specific examples of the organic substance are polymers such as polyethylene glycol, methyl cellulose, polyvinyl alcohol, polyacrylic acid and polyacrylamide.

Various effects may be attained by adding an inorganic substance and an organic substance, and principal effects are formation of the silica-based material into a spherical shape and control of the pore size and the pore volume thereof. More specifically, the liquid property of the mixed slurry is a significant factor for obtaining a spherical silica-based material. When an inorganic substance or an organic substance is added to adjust the viscosity and a solid content concentration of the slurry, the liquid property may be changed to easily obtain a spherical silica-based material. Furthermore, in order to control the pore size and the pore volume, an optimum organic compound that remains inside the silica-based material during its shape formation and may be removed through calcining and washing operations performed after the shape formation is selected.

Subsequently, the composition such as the slurry or the gel including various raw materials and additives, or the reactant is dried. A method for drying is not particularly limited, but spray drying is preferably employed from the viewpoint of controlling the particle size of the silica-based material. In this case, as a method for changing the mixed slurry into droplets, a method using a known atomizer of a rotary disk type, a two-fluid nozzle type, a pressurized nozzle type or the like may be used.

The liquid (slurry) to be sprayed should be in a well-mixed state. When it is in a poorly mixed state, performances of the silica-based material are harmfully affected, for example, durability is degraded, due to an uneven distribution of the composition. Viscosity increase or partial gelation (condensation of colloid) may be caused in the slurry particularly in mixing respective raw materials, which may lead to fears that ununiform particles may be formed. Therefore, in some cases, the mixed slurry is preferably prepared while controlling the mixture to be placed in, for example, a metastable state of a silica sol in the vicinity of pH 2 by, for example, carefully gradually mixing the raw materials with stirring as well as by adding an acid or an alkali.

The liquid to be sprayed preferably has viscosity and a solid content concentration respectively in prescribed ranges. When the viscosity and the solid content concentration are below the prescribed ranges, porous bodies obtained through the spray drying may not be in a perfect spherical shape but many of the porous bodies are liable to be formed in a depressed spherical shape. Alternatively, when they are beyond the prescribed ranges, dispersibility of the porous bodies may be harmfully affected, and in addition, droplets may not be stably formed depending upon the properties of the liquid. Therefore, the viscosity of the liquid to be sprayed is preferably in a range of 5 to 10000 cp at a temperature at the time of spraying as far as the liquid may be sprayed. Furthermore, from the viewpoint of the shape, higher viscosity within a sprayable range is liable to be preferred, and the viscosity is more preferably in a range of 10 to 1000 cp in consideration of balance with operability. Moreover, the solid content concentration is preferably in a range of 10 to 50% by mass from the viewpoint of the shape and the particle size. Incidentally, as a standard for spray drying conditions, it is preferred that a hot air temperature at an inlet of a drying chamber of a spray dryer is 200 to 280° C. and a temperature at an outlet of the drying chamber is 110 to 140° C.

Next, the composition obtained after drying the resultant substance of any of the methods (1) to (5) or the reactant obtained by the method (6) is calcined, so as to give a solid material. A calcining temperature is generally in a range of 200 to 800° C. When the composition is calcined at a temperature of 800° C. or less, the specific surface area of the silica-based material may be increased, and when the composition is calcined at a temperature of 200° C. or more, dehydration and condensation reaction among gels may be more sufficiently caused, and hence, the increase of the pore volume and bulk increase may be further suppressed. A calcining temperature in a range of 300 to 600° C. is preferable from the viewpoint of balance in the physical properties, the operability and the like. However, when the composition includes a nitrate, the composition is preferably calcined at a temperature exceeding a decomposition temperature of the nitrate. The physical properties of the silica-based material such as porosity may be varied in accordance with the calcining temperature and a temperature increase rate, and appropriate calcining temperature and temperature increase rate condition are selected in accordance with desired physical properties. In other words, when the calcining temperature is set to an appropriate condition, the composition may well retain the durability as a composite oxide and the decrease of the pore volume may be suppressed. Furthermore, as a temperature increase condition, the temperature is preferably gradually increased by utilizing programmed temperature increase or the like. In this manner, it is possible to prevent a problem in which an inorganic substance or an organic substance is vigorously gasified or combusted and hence a composition is liable to be exposed to a high temperature exceeding setting or liable to have cracks, and is crushed as a result.

The atmosphere for the calcining is not particularly limited, but the calcining is generally performed in the air or in nitrogen. Besides, time for the calcining may be determined in accordance with the specific surface area of the silica-based material attained after the calcining, and is generally 1 to 48 hours. The physical properties such as porosity of the silica-based material may be changed also in accordance with these calcining conditions, and the calcining conditions may be selected in accordance with desired physical properties.

The solid material obtained through the calcining step as described above may be used as the silica-based material of the present embodiment, but the solid material is preferably further subjected to a hydrothermal treatment. Through a step of the hydrothermal treatment, a silica-based material having a uniform porous structure in which pore sizes of most of pores fall in a remarkably narrow range of 3 to 5 nm and having a high specific surface area and high mechanical strength may be obtained.

The "hydrothermal treatment" herein means an operation to immerse the solid material in water or a solution including water and keep the solid material therein for a prescribed period of time while heating. The present inventors presume that a sufficient amount of water may be thus present in the pores of the solid material and mass transfer is caused with the water used as a medium so as to reconstitute the pores. Accordingly, from the viewpoint of accelerating rapid mass transfer, a temperature for the hydrothermal treatment is preferably 60° C. or more, more preferably 70° C. or more, further more preferably 80° C. or more and particularly preferably 90° C. or more. Although the temperature of the hydrothermal treatment may be as high as 100° C. or more, it is necessary to use a pressure device in this case so as not to allow excessive evaporation of moisture. Alternatively, although the silica-based material of the present embodiment may be obtained when the temperature of the hydrothermal treatment is as low as less than 60° C., time necessary for the treatment is liable to be long in this case. In addition, as is obvious from the above description, the hydrothermal treatment performed at a temperature exceeding a boiling point of the solution under increased pressure is advantageous for attaining the effects in short time. From the viewpoint of easiness in performing the operation, however, the hydrothermal treatment is preferably performed at a higher temperature within a range below the boiling point in general. Time of the hydrothermal treatment is varied depending upon conditions such as the kinds of metals included in the solid material, amounts of the metals, composition ratios of the metals, and the treatment temperature, but is preferably 1 minute to 5 hours, more preferably 5 minutes to 3 hours and further more preferably 5 minutes to 1 hour.

The reason why the pore distribution is narrowed through the hydrothermal treatment is not clear and has not been sufficiently examined in detail yet, but the present inventors currently presume the reason as follows: When a composition including silica as described above is molded, dried and calcined, a crosslinking reaction among particles in the composition is proceeded, and a structure (a solid material) having a pore distribution of 2 to 10 nm is first formed. Through the step of drying or the step of calcining, dehydration and crosslinkage among gels are proceeded by heating in a gas atmosphere, but since these reactions are solid phase reactions, the resultant silica-based material does not always attain a uniform pore distribution. When the solid material is further subjected to the hydrothermal treatment, however, a reaction of hydrolysis and re-crosslinkage of the solid material is proceeded, which probably causes recombination of the structure. Furthermore, considering that the pore volume thus attained is close to a void volume attained by closest packing of particles, it is presumed that the structure is changed to a thermodynamically stable packing structure through a hydrothermal reaction caused in the hydrothermal treatment, resulting in obtaining a silica-based material having a pore distribution in a narrow range of a pore size of 3 to 5 nm.

Next, another preferable process for producing the silica-based material of the present embodiment will be described. This production process includes a step of obtaining a solid material by calcining a composition including silica, an aluminum compound and a compound of at least one basic element selected from the group consisting of alkali metal elements, alkali earth metal elements and rare earth elements or calcining a dried substance of the composition (a first step); a step of causing a fourth period element to deposit on the solid material by neutralizing a mixture of the solid material and an acidic aqueous solution of a soluble metal salt including at least one fourth period element selected from the group consisting of iron, cobalt, nickel and zinc (a second step); a step of subjecting the solid material having the fourth period element deposited thereon to a hydrothermal treatment (a third step); and a step of heat-treating the solid material having been subjected to the hydrothermal treatment (a fourth step).

In the first step, a slurry including silica, an aluminum compound and a compound of the basic element is prepared, dried and then calcined, so as to give a solid material. The slurry may be prepared in the same manner as in the above-described method of the present embodiment except that a compound of a fourth period element is not included. Furthermore, the calcining temperature may be the same as that in the above-described method of the present embodiment.

Next, in the second step, a mixture of the solid material obtained in the first step and an acidic aqueous solution including the fourth period element is neutralized, whereby causing a component including the fourth period element to deposit on the solid material. At this point, the solid material to be mixed with the acidic aqueous solution may be in a state of a water slurry obtained by dispersing the solid material in water. At this stage, through a neutralization reaction caused between ions of the fourth period element and bases in the aqueous solution, the component including the fourth period element is deposited and fixed on the solid material in the form of, for example, a hydroxide of the fourth period element.

Examples of the base used in the neutralization in the second step are sodium hydroxide, potassium hydroxide, sodium carbonate, potassium carbonate and ammonia. Furthermore, the solid material or the water slurry including the solid material may include a component containing one of or two or more of basic elements selected from the group consisting of alkali metal elements (Li, Na, K, Rb, Cs), alkali earth metal elements (Be, Mg, Ca, Sr, Ba) and rare earth elements (La, Ce, Pr). Examples of the component containing such a basic element are potassium hydroxide, rubidium hydroxide, magnesium oxide, strontium oxide, lanthanum oxide and cerium oxide.

In the second step, for example, an acidic aqueous solution of a soluble metal salt including a fourth period element is mixed with the solid material and the mixture is neutralized with a base with stirring, so as to cause a component of the fourth period element to deposit on the solid material. In causing the component of the fourth period element to deposit, conditions such as a concentration of the acidic aqueous solution including the fourth period element, the base, the pH of the aqueous solution and the temperature may be appropriately selected.

The concentration of the fourth period element in the acidic aqueous solution (in case of including two or more fourth period elements, a concentration of each of the fourth period elements) is preferably 0.0001 to 1.0 mol/L, more preferably 0.001 to 0.5 mol/L, and further more preferably 0.005 to 0.2 mol/L.

When the neutralization is caused by using a base, the amount of the base may be adjusted so that the pH of the aqueous solution may be preferably 5 to 10 and more preferably 6 to 8. The temperature of the aqueous solution is preferably 0 to 100° C., more preferably 30 to 90° C. and further more preferably 60 to 90° C.

Time required for causing the deposition of the component including the fourth period element depends upon the contents of alumina, the fourth period element and the basic element and the conditions of the temperature and the like, and is preferably 1 minute to 5 hours, more preferably 5 minutes to 3 hours and further more preferably 5 minutes to 1 hour.

Subsequently, in the third step, the solid material having the component including the fourth period element deposited thereon is subjected to the hydrothermal treatment, whereby obtaining a mixture. When the solid material is subjected to the hydrothermal treatment, hydrolysis and re-crosslinkage of the silica gel are proceeded, and recombination of the structure is caused and at the same time, complexing of the compound of the fourth period element is proceeded.

The hydrothermal treatment may be the same as that described in the present embodiment, and the neutralized solution used in the second step may be directly heated for the hydrothermal treatment. The hydrothermal treatment is carried out preferably at a temperature of 60° C. or more for 1 to 48 hours. Although the hydrothermal treatment may be performed at a low temperature below 60° C., the treatment time is liable to be long in this case. From the viewpoint of the operability and the treatment time, the hydrothermal treatment is preferably carried out at 60 to 90° C.

Moreover, the solid material included in the mixture obtained in the third step is washed with water if necessary and dried, and then, is heat-treated in the fourth step. In this manner, the silica-based material of the present embodiment may be obtained.

The heat treatment temperature for the solid material in the fourth step is preferably 40 to 900° C., more preferably 80 to 800° C., further more preferably 200 to 700° C. and particularly preferably 300 to 600° C.

As for the atmosphere, the heat treatment is performed, for example, in the air (or in the atmosphere), in an oxidative atmosphere (including oxygen, ozone, nitrogen oxide, carbon dioxide, hydrogen peroxide, hypochlorous acid, an inorganic/organic peroxide or the like), or in an inert gas atmosphere (including helium, argon, nitrogen or the like). The heat treatment time may be appropriately selected in accordance with the heat treatment temperature and the amount of the solid material.

The silica-based material of the present embodiment may be suitably used for a pigment, a filler, an abrasive, a base for cosmetics, a support for a pesticide, a catalyst support, an adsorbent, a material for a film structure and the like.

Now, various uses will be specifically described. First, a pigment is required to be a fine powder insoluble in water, oil, an organic solvent and the like and have high mechanical strength. Spherical particles of the silica-based material of the present embodiment have high mechanical strength and are excellent in water resistance, oil resistance and organic solvent resistance, and therefore, may be suitably used as a pigment. Furthermore, smaller particles are generally used as a pigment, and hence, an average particle size is preferably 10 µm or less and more preferably 5 µm or less.

A synthetic silica filler conventionally used as a filler has a bulk density as low as 0.04 to 0.2 g/cm$^3$, and hence, it is inconvenient for transport and handling. The bulk density of the silica-based material of the present embodiment may be increased up to 0.9 to 1.2 g/cm$^3$, and hence, the disadvantage of the conventional synthetic silica filler may be overcome. Furthermore, since this silica-based material has high mechanical strength, it is useful as a reinforcing agent for increasing the strength of a polymer. Moreover, this silica-based material is also useful as a flatting agent or a viscosity modifier for a prepolymer of a vinyl chloride paste, an epoxy resin or a polyester resin.

The silica-based material of the present embodiment has abrasion resistance, measured in accordance with a method described later, preferably of 1.0% by mass/15 h or less, and therefore is useful as an abrasive. As an abrasive, the shape and the geometric property of the bulk density are significant. As compared with silica sand, pumice stone, diatom earth or the like, the silica-based material of the present embodiment has high mechanical strength, is in a spherical shape and has a high bulk density, and therefore, is excellent in properties as an abrasive. In addition, it is necessary to unify a particle size of an abrasive in accordance with a target to be abraded, and since the silica-based material has high mechanical strength, it is minimally broken or the like even through classification, and it may be formed into a spherical particle substance with a particle size suitable to a target to be abraded. When used as an abrasive, the average particle size may be set to various ranges in accordance with a target to be abraded, and is preferably 1 to 300 µm in general, and a particle size optimum for use is employed. The silica-based material of the present embodiment may be used as an abrasive useful for polishing glass or wood, removing rust, removing stain, finishing handiworks of metals, wood or bone such as ivory, and giving luster to artistic crafts, ceramics or soft metals.

A base for cosmetics is required to have high stability against a human body and have high usability. Since the silica-based material of the present embodiment is excellent in the water resistance, the oil resistance and the organic solvent resistance, it has high stability against a human body, and when it is in a spherical shape, it provides smooth feeling and has high usability, and therefore, it is useful as a base for cosmetics.

Particles used as a support for a pesticide preferably have a uniform particle size distribution, and particles of 10 µm or less are preferably removed through a treatment such as classification. When the particles of 10 m or less are removed, the physical properties of a powder material such as dustability, dispersibility, scatterability and stability over time may be remarkably improved.

The silica-based material of the present embodiment may be controlled in the pore size to fall in a range of 3 to 5 nm, and since it has a narrow pore size distribution, it may be effectively used as an ink adsorbent for ink jet printer paper. Furthermore, since the silica-based material of the present embodiment has a small pore volume and a high bulk density, the disadvantage of the conventional synthetic silica filler may be overcome, and since it has high mechanical strength, it is useful as a reinforcing agent for increasing the strength of a polymer. Moreover, the silica-based material of the present embodiment is useful also as a flatting agent or a viscosity modifier for a prepolymer of a vinyl chloride paste, an epoxy resin or a polyester resin.

The silica-based material may support various metal ions and may be used as a catalyst support. When it is used as a catalyst support, a catalytic active component is supported on the silica-based material, and the catalytic active component is appropriately selected in accordance with a target reaction. A metal component to be supported as an active component is preferably at least one noble metal component selected from the group consisting of ruthenium, rhodium, palladium, silver, rhenium, osmium, iridium, platinum and gold. More preferable one among the noble metal components is at least one selected from the group consisting of ruthenium, palladium, platinum and gold. One of the noble metal components may be singly used or a combination of two or more of them may be used. A chemical state of the noble metal component may be any one of a single metal, an oxide, a hydroxide, a composite compound including two or more noble metal elements and a mixture of them, and a preferable chemical state is a single metal or a metal oxide.

Noble metal particles are preferably supported on a support in a highly dispersed state. Specifically, the noble metal particles are supported preferably in a state where the particles do not overlap one another in a stacking direction on the support, and are supported to be dispersed more preferably in a particulate state (namely, a state where the particles are not in contact with one another) or in a thin film state (namely, a state where the particles do not overlap one another in the stacking direction on the support although they are in contact with one another). The noble metal particles have an average particle size of preferably 2 to 10 nm, more preferably 2 to 8 nm, and further more preferably 2 to 6 nm.

When the average particle size of the noble metal particles falls in the aforementioned range, a specific active species structure is formed, and hence, reaction activity is liable to be improved. The term "average particle size" herein means a number average particle size measured by using a transmission electron microscope (TEM). Specifically, in an image observed with a transmission electron microscope, black contrast portions correspond to composite particles, and diameters of all the particles within the image are measured so as to calculate an average particle size as an average of the measured values.

The noble metal-supported material may include a second component element in addition to the noble metal component. The second component element is at least one metal selected from the group consisting of elements belonging to group IV to XVI of the fourth, fifth and sixth periods in the periodic table. Specific examples of the second component element are titanium, vanadium, chrome, manganese, iron, cobalt, nickel, copper, zinc, gallium, zirconium, niobium, molybdenum, cadmium, indium, tin, antimony, tellurium, hafnium, tungsten, iridium, mercury, thallium, lead and bismuth. Furthermore, as the second component element, alkali metals, alkali earth metals and rare earth metals may be included.

One of these metal elements may be singly used or a combination of two or more of them may be used. A chemical state of such a metal element may be any one of a single metal, an oxide, a hydroxide, a composite compound including two or more metal elements or a mixture of them, and a preferable chemical state is a single metal or a metal oxide.

An amount of each noble metal component to be supported is not particularly limited. In the case where at least one noble metal element selected from the group consisting of ruthenium, rhodium, palladium, silver, rhenium, osmium, iridium, platinum and gold is supported, the amount of these metals to be supported is preferably 0.1 to 20% by mass in total and more preferably 1 to 10% by mass in total based on 100% by mass of the support. The noble metal component may be a single noble metal or a compound (such as an oxide or a hydroxide) of the noble metal element.

In the case where at least one metal element selected from the group consisting of elements belonging to group IV to XVI of the fourth, fifth and sixth periods in the periodic table and/or a compound of such a metal element is supported, the amount of the element to be supported is preferably 0.01 to 20% by mass in total and more preferably 0.05 to 10% by mass per mass of the noble metal-supported material. In the case where alkali metals, alkali earth metals and rare earth metals are supported, the amount of these metals to be supported is preferably 0.5 to 30% by mass in total and more preferably 1 to 15% by mass per mass of the noble metal-supported material.

The noble metal-supported material of the present embodiment has a specific surface area, measured by a BET nitrogen adsorption method, of preferably 20 to 500 $m^2/g$, more preferably 50 to 400 $m^2/g$ and further more preferably 100 to 350 $m^2/g$ from the viewpoint that reaction activity is improved and that active components are minimally released.

A pore structure of the noble metal-supported material of the present embodiment is one of extremely significant physical properties from the viewpoint of characteristics for supporting noble metal components, long-term stability including stability against peeling, and reaction characteristics obtained when used as a catalyst, and a pore size is a physical property corresponding to an indicator for developing these characteristics. When the pore size is smaller than 3 nm, a peeling property for a supported noble metal component is liable to be good, but when used in a liquid phase reaction or the like as a catalyst, diffusion resistance of a reaction matrix within pores is increased, a diffusion process of the reaction matrix easily becomes rate-determining, and hence, the reaction activity is liable to be lowered. Therefore, the pore size is preferably 3 nm or more. On the other hand, the pore size is preferably 50 nm or less from the viewpoint that the support is difficult to break and that supported noble metal particles are difficult to peel off. Accordingly, the pore size of the noble metal-supported material is preferably 3 nm to 50 nm, more preferably 3 nm to 30 nm and further more preferably 3 nm to 10 nm. A pore volume is, from the viewpoint of the supporting characteristics and reaction characteristics, in a range of preferably 0.1 to 1.0 mL/g, more preferably 0.1 to 0.5 mL/g and further more preferably 0.1 to 0.3 mL/g. The noble metal-supported material of the present embodiment preferably has a pore size and a pore volume both meeting the aforementioned ranges.

A method for causing the silica-based material to support a noble metal component is not particularly limited as far as the aforementioned support may be obtained, and a generally employed production process for a metal-supported material, such as impregnation (including adsorption, pore-filling, evaporation to dryness and spraying), precipitation (including coprecipitation, deposition and kneading), ion exchange and vapor deposition, may be applied. Although metal components other than a noble metal may be added during the preparation of the noble metal-supported material, when the noble metal-supported material is used as a catalyst, the metal components may be added to a reaction system using the catalyst.

In the case where a second component element is included in addition to a noble metal component, the second component element may be added to the noble metal-supported material during the preparation or the reaction of the noble metal-supported material or may be preliminarily included in the support. It is noted that the structure of a second component element within the noble metal-supported material is not particularly limited, and it may form, together with the noble metal particles, an alloy or an intermetallic compound, or may be supported on the support separately from the noble metal particles. Also an alkali metal compound or an alkali earth metal compound may be preliminarily allowed to coexist during the preparation of the noble metal-supported material, or may be added during the preparation of the noble metal-supported material or to the reaction system. As a metal raw material used in the preparation of the catalyst, a compound such as inorganic compounds or organic compounds of the metals described above may be used, and preferable examples are metallic halides, metal oxides, metal hydroxides, metal nitrates, metal sulfates, metal acetates, metal phosphates, metal carbonyl, metal acetylacetonate, metal porphyrins and metal phthalocyanines.

[Process for Preparing Noble Metal-Supported Material Including Second Component Element in Addition to Noble Metal Component]

A process for preparing a noble metal-supported material including a second component element in addition to a noble metal component will now be described by exemplifying the precipitation. First, as a first step, for example, an acidic aqueous solution of a soluble metal salt including a second component and a noble metal is neutralized for depositing the second component and the noble metal component on the silica-based material, whereby obtaining a precursor of a noble metal-supported material. At this stage, the second component and the noble metal component (such as a hydroxide) are deposited and fixed on the silica-based material through the neutralization reaction caused between ions of the second component and the noble metal with a base within the aqueous solution. Subsequently, in a second step, the precursor of the noble metal-supported material obtained in the first step is washed with water if necessary and dried, and thereafter, subjected to a heat treatment, so as to give the noble metal-supported material.

Examples of the soluble metal salt including the second component element used in the preparation of the noble metal-supported material are nitrate, acetate and chloride of the second component element. Furthermore, examples of the soluble metal salt including the noble metal component are, when palladium is selected as the noble metal, palladium chloride and palladium acetate, when ruthenium is selected, ruthenium chloride and ruthenium nitrate, when gold is selected, chloroauric acid, gold sodium chloride, potassium dicyanoaurate, diethylamine gold trichloride and gold cyanide, and when silver is selected, silver chloride and silver nitrate.

As the base for use in the preparation of the noble metal-supported material, sodium hydroxide, potassium hydroxide, sodium carbonate, potassium carbonate, ammonia and the like are used. Furthermore, the support may include one of or a plurality of basic metal components selected from the alkali metals (Li, Na, K, Rb, Cs), the alkali earth metals (Be, Mg, Ca, Sr, Ba) and rare earth metals (La, Ce, Pr).

In the first step, the acidic aqueous solution of a soluble metal salt including a second component element and a noble metal is mixed with the silica-based material, and the resultant mixture is neutralized by a base with stirring, so as to deposit precipitate of the second component element and the noble metal component on the silica-based material. In depositing the second component element and the noble metal element, conditions such as a concentration of the aqueous solution including the second component element and the noble metal element, the base, the pH of the aqueous solution, the temperature and the like may be appropriately selected.

Concentrations of the second component element and the noble metal in the aqueous solution are generally 0.0001 to 1.0 mol/L, preferably 0.001 to 0.5 mol/L, more preferably 0.005 to 0.2 mol/L. A ratio between the second component element and the noble metal in the aqueous solution is in a range of preferably 0.1 to 10, more preferably 0.2 to 5.0 and further more preferably 0.5 to 3.0 in terms of a second component element/noble metal atomic ratio.

The pH of the aqueous solution may be adjusted by using the base so as to be in a range of generally 5 to 10 and preferably 6 to 8. The temperature of the aqueous solution is generally 0 to 100° C., preferably 30 to 90° C. and more preferably 60 to 90° C.

Time for the deposition of the second component element and the noble metal component is not particularly limited and is varied depending upon the kind of silica-based material, the amounts of the second component element and the noble metal to be supported and the ratio therebetween, and the like, and is generally 1 minute to 5 hours, preferably 5 minutes to 3 hours and more preferably 5 minutes to 1 hour.

A heat treatment temperature for the precursor of the noble metal-supported material employed in the second step is generally 40 to 900° C., preferably 80 to 800° C., more preferably 200 to 700° and further more preferably 300 to 600° C.

As for the atmosphere, the heat treatment is performed in the air (or in the atmosphere), in an oxidative atmosphere (including oxygen, ozone, nitrogen oxide, carbon dioxide, hydrogen peroxide, hypochlorous acid, an inorganic/organic peroxide or the like), or in an inert gas atmosphere (including helium, argon, nitrogen or the like). The time for the heat treatment may be appropriately selected in accordance with the heat treatment temperature and the amount of the precursor of the noble metal-supported material.

After the second step described above, a reduction treatment may be performed in a reductive atmosphere (including hydrogen, hydrazine, formalin, formic acid or the like) if necessary. The temperature and the time of the reduction treatment may be appropriately selected in accordance with the kind of reducing agent, the kind of noble metal and the amount of the noble metal-supported material.

After the heat treatment or the reduction treatment, an oxidation treatment may be performed in the air (or in the atmosphere) or in an oxidative atmosphere (including oxygen, ozone, nitrogen oxide, carbon dioxide, hydrogen peroxide, hypochlorous acid, an inorganic/organic peroxide or the like) if necessary. In this case, the temperature and the time may be appropriately selected in accordance with the kind of oxidant, the kind of noble metal and the amount of the noble metal-supported material.

[Process for Preparing Compound Using Noble Metal-Supported Material as Catalyst]

The noble metal-supported material of the present embodiment is used as a catalyst widely for chemical synthesis. The noble metal-supported material is used as, for example, a chemical synthesis catalyst for oxidation of alkane, oxidation of alcohol, oxidation of aldehyde, oxidation of carbonyl, oxidation of alkene, epoxidation of alkene, oxidative addition of alkene, oxidative esterification of aldehyde and alcohol, oxidative esterification of alcohol, oxidative esterification of glycol and alcohol, hydrogenation of alkene, hydrogenation of alkyne, hydrogenation of phenols, a selective hydrogenation reaction of $\alpha,\beta$ unsaturated ketone, a hydrogenation reaction of nitro, olefin, carbonyl, an aromatic ring or the like, amination, direct hydrogen peroxide synthesis from hydrogen and oxygen, oxidation of carbon monoxide, a water gas shift reaction or the like, or as a reduction catalyst for Nox, or a photocatalyst.

Now, a process for producing carboxylic acid ester from aldehyde and alcohol through an oxidative esterification reaction performed in the presence of oxygen by using the noble metal-supported material of the present embodiment as a catalyst will be exemplarily described.

Examples of the aldehyde used as a raw material are C1-C10 saturated aliphatic aldehydes such as formaldehyde, acetaldehyde, propionaldehyde, isobutyl aldehyde and glyoxal; C3-C10 $\alpha,\beta$-unsaturated aliphatic aldehydes such as acrolein, methacrolein and crotonaldehyde; C6-C20 aromatic aldehydes such as benzaldehyde, tolyl aldehyde, benzilaldehyde and phthalaldehyde; and derivatives of these aldehydes. One of these aldehydes is singly used or a mixture of two or more of them is used. When the aldehyde is at least one selected from the group consisting of acrolein, methacrolein and a mixture of them, the noble metal-supported material of the present embodiment may be further effectively used as a catalyst.

Examples of the alcohol are C1-C10 saturated aliphatic alcohols such as methanol, ethanol, isopropanol, butanol, 2-ethyl hexanol and octanol; C5-C10 alicyclic alcohols such as cyclopentanol and cyclohexanol; C2-C10 diols such as ethylene glycol, propylene glycol and butane diol; C3-C10 unsaturated aliphatic alcohols such as allyl alcohol and methallyl alcohol; C6-C20 aromatic alcohols such as benzyl alcohol; and hydroxyoxetane such as 3-alkyl-3-hydroxymethyloxetane. One of these alcohols is singly used or a mixture of two or more of them is used. The alcohol is preferably methanol among these examples because thus, the noble metal-supported material of the present embodiment may be further effectively used as a catalyst.

A content ratio between the aldehyde and the alcohol is not particularly limited, and for example, a ratio (aldehyde/alcohol) of the aldehyde to the alcohol on a mole basis may be in a wide range of 10 to 1/1000 but is generally 1/2 to 1/50.

A usage of the catalyst may be largely varied depending upon the kinds of reaction raw materials, the composition and the preparation process of the catalyst, reaction conditions, a reaction type and the like, and is not particularly limited. In the case where the catalyst is reacted in a slurry state, the catalyst is used in a solid content concentration, in the slurry, of preferably 1 to 50 mass/vol %, more preferably 3 to 30 mass/vol % and further more preferably 10 to 25 mass/vol %.

The production of carboxylic acid ester may be performed by employing an arbitrary method such as a gas phase reaction, a liquid phase reaction or a trickle reaction and employing any of a batch production system and a series production system.

The reaction may be performed without a solvent but may be performed with a solvent inert to reaction components (of a reaction matrix, a reaction product and a catalyst), such as hexane, decane, benzene and dioxane.

A reaction type may be any of conventionally known types such as a fixed bed type, a fluid bed type, a stirred tank type and the like. When the reaction is conducted, for example, in a liquid phase, an arbitrary type reactor such as a bubbling column reactor, a draft tube type reactor or a stirred tank reactor may be employed.

Oxygen used in the production of carboxylic acid ester may be in the form of molecular oxygen, namely, an oxygen gas itself or a mixed gas obtained by diluting an oxygen gas with a diluent inert to the reaction, such as nitrogen or carbon dioxide gas. As an oxygen raw material, the air is preferably used from the viewpoint of operability, economy and the like.

An oxygen partial pressure is varied depending upon the reaction raw materials of aldehyde species, alcohol species and the like, reaction conditions or the reactor type and the like, and practically, an oxygen partial pressure at an outlet of a reactor is set to fall in a range of a concentration below a lower limit of an explosive range, and is preferably controlled to be, for example, 20 to 80 kPa. A reaction pressure may be in an arbitrary wide range from reduced pressure to increased pressure, and is in a range of, for example, 0.05 to 2 MPa. Furthermore, a total pressure is preferably set so that an oxygen concentration in a gas flowing out of the reactor may not exceed an explosive limit (so that the oxygen concentration may be, for example, 8%) from the viewpoint of safety.

When the production reaction for carboxylic acid ester is conducted in a liquid phase or the like, pH of the reaction system is preferably kept at 6 to 9 by adding compounds (such as oxides, hydroxides, carbonates and carboxylates) of alkali metals or alkali earth metals to the reaction system. One of such compounds of the alkali metals or the alkali earth metals is singly used, or a combination of two or more of them is used.

The reaction temperature in the production of carboxylic acid ester may be a high temperature exceeding 200° C. but is preferably 30 to 200° C., more preferably 40 to 150° C. and further more preferably 60 to 120°. The reaction time is not particularly limited and may not be uniquely determined because it depends upon set conditions, and is generally 1 to 20 hours.

Next, a process for producing carboxylic acid through oxidation of aldehyde in a liquid phase including water by using the noble metal-supported material of the present embodiment as a catalyst will be exemplarily described.

The water included in the liquid phase is not particularly limited, and examples are soft water, purified industrial water and ion-exchanged water. Any water may be used as far as it has general water quality, but one including a large amount of impurity (such as ions of Fe, Ca, Mg and the like) is unpreferable. Examples of the aldehyde used in the production of carboxylic acid are C1-C10 saturated aliphatic aldehydes such as formaldehyde, acetaldehyde, propionaldehyde, isobutyl aldehyde and glyoxal; C3-C10 α,β-unsaturated aliphatic aldehydes such as acrolein, methacrolein and crotonaldehyde; C6-C20 aromatic aldehydes such as benzaldehyde, tolyl aldehyde, benzilaldehyde and phthalaldehyde; and derivatives of these aldehydes. Among these aldehydes, methacrolein and acrolein are preferred. One of these aldehydes may be singly used or a combination of arbitrary two or more of them may be used.

A content ratio between the aldehyde and the water is not particularly limited, and an aldehyde/water mole ratio may be in a wide range of, for example, 1/10 to 1/1000, but is generally in a range of 1/2 to 1/100.

It is possible to oxidize the aldehyde in a mixed liquid phase including the aldehyde and the water, namely, under conditions with no solvent, but a solvent may be added to the mixed liquid of the aldehyde and the water so as to obtain a mixed liquid of the aldehyde, the water and the solvent. As the solvent, for example, ketones, nitriles, alcohols, organic esters, hydrocarbons, organic acids and amides may be used. Examples of the ketones are acetone, methyl ethyl ketone and methyl isobutyl ketone. Examples of the nitriles are acetonitrile and propionitrile. Examples of the alcohols are tertiary butanol and cyclohexanol. Examples of the organic acid esters are ethyl acetate and methyl propionate. Examples of the hydrocarbons are hexane, cyclohexane and toluene. Examples of the organic acids are acetic acid, propionic acid, n-butyric acid, isobutyric acid, n-pentanoic acid and isovaleric acid. Examples of the amides are N,N-dimethylformamide, N,N-dimethylacetamide, N,N-dimethylpropionamide and hexamethylphosphoramide. Furthermore, a single solvent may be used or a mixed solvent composed of two or more solvents may be used. In the case where the water and the solvent are mixed, a mixing ratio is not particularly limited because it may largely varied depending upon the kind of aldehyde used as a reaction raw material, the composition and the preparation process of the catalyst, reaction conditions, reaction type and the like, but from the viewpoint of producing carboxylic acid from aldehyde with high selectivity and high productivity, the amount of solvent is preferably 8 to 65% by mass and more preferably 8 to 55% by mass based on the mass of the water. The mixed liquid of the aldehyde and the water or the mixed liquid of the aldehyde, the water and the solvent is preferably homogenous but may be used in an inhomogeneous state.

A usage of the catalyst may be largely varied depending upon the kind of reaction raw material, the composition and the preparation process of the catalyst, the reaction conditions, the reaction type and the like and is not particularly limited, but when the catalyst is reacted in a slurry state, it is used in a range of preferably 4 to 50 mass/vol %, more preferably 4 to 30 mass/vol % and further more preferably 10 to 25 mass/vol % in terms of a catalyst concentration in the slurry. In other words, the catalyst is used so that a ratio of the mass (kg) of the catalyst to the volume (L) of the liquid component may fall in a range of preferably 4 to 50%, more preferably 4 to 30% and further more preferably 10 to 25%.

The production of carboxylic acid in a liquid phase may be performed by employing any of the series production system and the batch production system, but the series production system is industrially preferred in consideration of the productivity.

As an oxygen source for oxidation, an oxygen gas itself may be supplied to a reactor, or a mixed gas obtained by diluting an oxygen gas with a diluent inert to the reaction, such as nitrogen or carbon dioxide gas, may be supplied, and the air is suitably used as the oxygen source from the viewpoint of operability, economy and the like.

A preferable oxygen partial pressure is varied depending upon aldehyde species, solvent species, reaction conditions or a reactor type and the like, and practically, an oxygen partial pressure at an outlet of a reactor is set to fall in a range of a concentration below a lower limit of an explosive range, and is preferably controlled to be, for example, 20 to 80 kPa. A reaction pressure may be in an arbitrary wide range from reduced pressure to increased pressure, and is generally 0.05 to 5 MPa. From the viewpoint of safety, a total pressure is preferably set so that an oxygen concentration in a gas flowing out of the reactor may not exceed an explosive limit (8%).

The reaction temperature for the production of carboxylic acid is preferably 30 to 200° C., more preferably 40 to 150° C. and further more preferably 60 to 120°. The reaction time is not particularly limited and is generally 1 to 20 hours.

Incidentally, determination of contents of composing elements of the silica-based material (Si, Al, a fourth period element and a basic element), determination of a composition ratio of the fourth period element to the aluminum or the basic element, measurement of a specific surface area, a pore size and a pore volume, observation of a shape, measurement of an average particle size, measurement of a bulk density (CBD), measurement of abrasion resistance, analysis of a crystal structure, analysis of a chemical state of the fourth period element, and observation of form of a noble metal-supported material may be carried out as follows:

[Determination of Contents of Composing Elements of Silica-Based Material and Noble Metal-Supported Material]

Concentrations of Si, Al, a fourth period element and a basic element in a silica-based material are determined by using "IRIS Intrepid II XDL" (trade name), that is, an ICP emission spectrophotometric analyzer (ICP-AES, MS) manufactured by Thermo Fisher Scientific Inc.

A sample is prepared as follows: First, a silica-based material is weighed in a Teflon (registered trademark) decomposition vessel, and nitric acid and hydrogen fluoride are added thereto. The thus obtained solution is thermally decomposed by "ETHOS TC" (trade name), that is, a microwave decomposition apparatus manufactured by Milestone General K.K., and thereafter, the thus decomposed substance is evaporated to dryness on a heater. Subsequently, nitric acid and hydrochloric acid are added to the thus deposited residue, the resultant mixture is pressure decomposed by the microwave decomposition apparatus, pure water is added to the thus obtained decomposed solution into a given volume, and the resultant solution is used as a sample.

The sample is quantitatively determined by an internal standard method by using the ICP-AES, and contents of Si, Al, a fourth period element and a basic element in a silica-based material and contents of metal elements in a noble metal-supported material are obtained by subtracting a measurement blank value simultaneously obtained, so as to calculate a composition ratio (on a mole basis) and an amount of supported metal.

[Determination of Composition Ratio]

On the basis of the contents of Al, the fourth period element and the basic element measured as described in "Determination of Contents of Composing Elements of Silica-based Material and Noble Metal-Supported Material," a composition ratio (X/Al) of the fourth period element to the aluminum and a composition ratio (X/B) of the fourth period element to the basic element are calculated.

[Measurement of Specific Surface Area, Pore Size and Pore Volume]

Specific surface areas, pore sizes and pore volumes of a silica-based material and a noble metal-supported material are measured, with nitrogen used as an adsorption gas, with "Autosorb 3MP" (trade name), that is, a gas adsorption measuring apparatus manufactured by Yuasa Ionics Inc. (nitrogen adsorption method). A specific surface area is obtained by the BET method, a pore size and a pore distribution are obtained by the BJH method, and a pore volume is obtained from an adsorption amount attained at P/P0 at max.

[Observation of Shape]

An X-650 scanning electron microscope (SEM) manufactured by Hitachi, Ltd. is used for observing particles of a silica-based material (a support) and a noble metal-supported material (a catalyst).

[Measurement of Average Particle Size]

Average particle sizes (on a volume basis) of a silica-based material and a noble metal-supported material are measured by using an LS230 laser diffraction scattering particle size analyzer manufactured by Beckman-Coulter, Inc.

[Measurement of Bulk Density (CBD)]

As a pretreatment, approximately 120 g of a silica-based material is first collected in a stainless steel crucible and calcined in a muffle furnace at 500° C. for 1 hour. The calcined silica-based material is placed in a desiccator (containing a silica gel) to be cooled to room temperature. The thus pretreated silica-based material is collected by 100.0 g and transferred to a 250 mL measuring cylinder, and the silica-based material is filled in the measuring cylinder while tapping for 15 minutes by using a shaker. The measuring cylinder is removed from the shaker, a surface of the silica-based material in the measuring cylinder is smoothed, and a packed volume is read. A bulk density is a value obtained by dividing the mass of the silica-based material by the packed volume.

[Measurement of Abrasion Resistance]

Approximately 50 g of a silica-based material is precisely weighed and introduced to a vertical tube with an inner diameter of 1.5 in. having, on a bottom thereof, a perforated disk with three orifices of 1/64 in. The air is externally blown into the vertical tube through the perforated disk at a rate of 15 CF (cubic feet)/h, so as to vigorously flow particles of the silica-based material in the tube. A ratio (% by mass) of a total amount of silica-based material particles that have been refined to be scattered and lost from an upper portion of the vertical tube to the amount thereof initially introduced is obtained as "abrasion resistance" in 5 to 20 hours after the air is blown into the vertical tube.

[Analysis of Crystal Structure]

A crystal structure of a silica-based material is analyzed by using "Rint 2500" (trade name), that is, a powder X-ray diffractometer (XRD) manufactured by Rigaku Corporation under conditions of an X-ray source of a Cu tube (40 kV, 200 mA), a measurement range of 5 to 65 deg. (0.02 deg/step), a measurement rate of 0.2 deg/min, and slit widths (for scattering, divergence and receiving) of 1 deg., 1 deg. and 0.15 mm.

For the measurement, a sample is uniformly spread over a reflection free sample holder and fixed with neoprene rubber.

[Analysis of Chemical State of Fourth Period Element (Nickel)]

A NiKα spectrum of a silica-based material is measured by an XFRA190 high-resolution X-ray fluorescence analyzer (HRXRF) manufactured by Technos Corp., various parameters thus obtained are compared with those of standard reference materials (nickel metal and nickel oxide), so as to estimate a chemical state such as a valence of nickel included in the silica-based material.

As a sample for the measurement, a prepared silica-based material is directly used. The NiKα spectrum is measured in a partial spectral mode. At this point, Ge (220) is used as dispersive crystal, a slit with a vertical divergence angle of 1° is used, and excitation voltage and current are respectively set to 35 kV and 80 mA. In addition, filter paper is used as an absorber for a standard sample, and count time is selected for each silica-based material sample, so that a Kα spectrum has peak intensity of 3000 cps or less and 10000 counts or more in the measurement. Each sample is repeatedly subjected to the measurement by five times, and before and after the repeated measurement, nickel metal is measured. After subjecting actually measured spectra to smoothing processing (an S-G method, 7 points, 5 times), peak positions, a half value width (FWHM) and asymmetry indexes (AI) are calculated, and each of the peak positions is dealt with as a shift, a chemical shift (ΔE), from the measured values of the nickel metal obtained before and after the measurement of each sample.

[Observation of Dispersion State of Fourth Period Element]

A cross-section of a silica-based material is analyzed by using EPMA 1600, manufactured by Shimadzu Corporation, at an acceleration voltage of 20 KeV.

[Observation of Form of Metal-Supported Material]

A TEM bright field image is observed with a 3100 FEF transmission electron microscope (TEM) manufactured by JEOL Ltd. [an acceleration voltage of 300 kV, equipped with an energy dispersive X-ray spectroscopy (EDX)].

For preparing a sample, a noble metal-supported material is ground with a mortar, dispersed in ethanol, and subjected to ultrasonic cleaning for approximately 1 minute, and the resultant is dropped onto a Mo microgrid and air dried.

EXAMPLES

The present invention will now be described in further detail by way of examples, but the present invention is not limited to these examples. It will be obvious for those skilled in the art that the present invention may be various modified and changed apart from the examples, and all changes and modifications are intended to be embraced by the appended claims. Incidentally, the determination of contents of composing elements of a silica-based material, the determination of a composition ratio of a fourth period element to aluminum or a basic element, the measurement of a specific surface area, a pore size and a pore volume, the observation of a shape, the measurement of an average particle size, the measurement of a bulk density, the measurement of abrasion resistance, the analysis of a crystal structure, the analysis of a chemical state of the fourth period element, and the observation of form of a noble metal-supported material are carried out as described above in each of examples and comparative examples.

Example 1

An aqueous solution of 1.5 kg of aluminum nitrate nonahydrate, 0.24 kg of nickel nitrate hexahydrate, 0.98 kg of magnesium nitrate hexahydrate and 0.27 kg of 60% nitric acid dissolved in 3.0 L of pure water was prepared. The aqueous solution was gradually added dropwise to 10.0 kg of a silica sol solution (trade name "Snowtex N-30" manufactured by Nissan Chemical Industries Ltd., $SiO_2$ content: 30% by mass) kept at 15° C. with stirring and having a colloidal particle size of 10 to 20 nm, so as to give a mixed slurry of a silica sol, aluminum nitrate, nickel nitrate and magnesium nitrate. Thereafter, the mixed slurry was spray dried with a spray dryer with an outlet temperature set to 130° C. to obtain a solid material.

Subsequently, the thus obtained solid material was filled into a thickness of approximately 1 cm within a stainless steel vessel having an open top, and was heated in an electric furnace with a temperature increased from room temperature to 300° C. over 2 hours and kept at 300° C. for 3 hours. The temperature was further increased to 600° C. over 2 hours and was kept at 600° C. for 3 hours for calcining. Thereafter, the solid material was slowly cooled, so as to obtain a silica-based material made of a composite oxide comprising silicon-aluminum-nickel-magnesium.

The obtained silica-based material was found to include 85.3 mol % of silicon, 6.8 mol % of aluminum, 1.4 mol % of nickel and 6.5 mol % of magnesium based on a total mole of silicon, aluminum, nickel and magnesium. The Ni(X)/Al composition ratio was 0.21 on a mole basis and the Ni(X)/Mg(B) composition ratio was 0.22 on a mole basis.

The specific surface area measured by the nitrogen adsorption method was 223 m$^2$/g, the pore volume was 0.26 mL/g and the average pore size was 5.1 nm. The bulk density was 0.97 CBD and the abrasion resistance was 0.1% by mass. The average particle size was found to be 62 μm on the basis of a result of laser scattering particle size distribution measurement. Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of powder X-ray diffraction (XRD).

The chemical state of nickel included in the silica-based material was presumed, on the basis of a result of the high-resolution X-ray fluorescence (HRXRF) spectroscopy, to be a high-spin state of nickel having a valence of 2, and was found, from a difference in the NiKα spectrum, to be different from a chemical state of nickel oxide, that is, a single compound. The half value width (FWHM) of the NiKα spectrum of the silica-based material obtained from an actually measured spectrum was 3.474, and the chemical shift (ΔE) was 0.331. As for nickel oxide measured as a standard reference material, the half value width (FWHM) of the NiKα spectrum was 3.249 and the chemical shift (ΔE) was 0.344.

As for a dispersion state of nickel in the silica-based material, it was found, from a result of the electron probe microanalysis (EPMA), that the nickel was present in substantially the same concentration in all portions.

Next, for evaluating resistance to acids and bases of the silica-based material, a pH swing test was performed as follows:

After adding 10 g of the silica-based material obtained as described above to 100 mL of a buffer solution of pH 4 contained in a glass vessel, the resultant solution was stirred for 10 minutes at 90° C. and then allowed to stand still for removing a supernatant, and the thus obtained precipitate was washed with water and decanted. The thus obtained solid material was added to 100 mL of a buffer solution of pH 10 contained in a glass vessel, the resultant solution was stirred for 10 minutes at 90° C. and then allowed to stand still for removing a supernatant, and the thus obtained precipitate was washed with water and decanted. With this operation regarded as one cycle, a pH swing process of 50 cycles in total was performed. As a result, after the pH swing process, the silica-based material had a specific surface area of 220 m$^2$/g, a pore volume of 0.27 mL/g and an average pore size of 5.2 nm, which reveals that the structure of the silica-based material had not been changed through the pH swing process.

Example 2

A silica-based material including 69.7 mol % of silicon, 15.0 mol % of aluminum, 0.5 mol % of zinc and 14.9 mol % of potassium was obtained in the same manner as in Example 1 except that 4.0 kg of aluminum nitrate nonahydrate was used instead of 1.5 kg of aluminum nitrate nonahydrate, 0.11 kg of zinc nitrate hexahydrate was used instead of 0.24 kg of nickel nitrate hexahydrate and 1.1 kg of potassium nitrate was used instead of 0.98 kg of magnesium nitrate hexahydrate. The Zn(X)/Al composition ratio was 0.03 on a mole basis and the Zn(X)/K(B) composition ratio was 0.03 on a mole basis. The specific surface area measured by the nitrogen adsorption method was 170 m$^2$/g, the pore volume was 0.27 mL/g and the average pore size was 5.3 nm. The bulk density was 0.95 CBD and the abrasion resistance was 0.1% by mass. The average particle size was found to be 64 μm on the basis of a result of the laser scattering particle size distribution measurement.

Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-based material obtained as described above, the pH swing test was performed in the same manner as in Example 1. As a result, after the pH swing process, the silica-based material had a specific surface area of 169 m$^2$/g, a pore volume of 0.26 mL/g and an average pore size of 5.7 nm, which reveals that the structure of the silica-based material had been minimally changed through the pH swing process.

Example 3

A silica-based material including 82.7 mol % of silicon, 8.8 mol % of aluminum, 4.3 mol % of cobalt and 4.3 mol % of rubidium was obtained in the same manner as in Example 1 except that 2.0 kg of aluminum nitrate nonahydrate was used instead of 1.5 kg of aluminum nitrate nonahydrate, 0.75 kg of cobalt nitrate hexahydrate was used instead of 0.24 kg of nickel nitrate hexahydrate and 0.38 kg of rubidium nitrate was used instead of 0.98 kg of magnesium nitrate hexahydrate. The Co(X)/Al composition ratio was 0.49 on a mole basis and the Co(X)/Rb(B) composition ratio was 0.99 on a mole basis. The specific surface area measured by the nitrogen adsorption method was 196 m$^2$/g, the pore volume was 0.26 mL/g and the average pore size was 5.1 nm. The bulk density was 0.96 CBD and the abrasion resistance was 0.1% by mass. The average particle size was found to be 62 μm on the basis of a result of the laser scattering particle size distribution measurement. Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

As for a dispersion state of cobalt in the silica-based material, it was found, from a result of the electron probe microanalysis (EPMA), that the cobalt was present in substantially the same concentration in all portions.

Next, for evaluating the resistance to acids and bases of the silica-based material obtained as described above, the pH swing test was performed in the same manner as in Example 1. As a result, after the pH swing process, the silica-based material had a specific surface area of 198 m$^2$/g, a pore volume of 0.26 mL/g and an average pore size of 5.0 nm, which reveals that the structure had not been changed through the pH swing process.

Example 4

A silica-based material including 89.9 mol % of silicon, 7.2 mol % of aluminum, 0.9 mol % of iron and 2.0 mol % of lanthanum was obtained in the same manner as in Example 1 except that 0.2 kg of iron nitrate nonahydrate was used instead of 0.24 kg of nickel nitrate hexahydrate and 0.48 kg of lanthanum nitrate nonahydrate was used instead of 0.98 kg of magnesium nitrate hexahydrate. The Fe(X)/Al composition ratio was 0.12 on a mole basis and the Fe(X)/La(B) composition ratio was 0.45 on a mole basis. The specific surface area measured by the nitrogen adsorption method was 232 m$^2$/g, the pore volume was 0.28 mL/g and the average pore size was 5.0 nm. The bulk density was 0.98 CBD and the abrasion resistance was 0.1% by mass. The average particle size was found to be 64 μm on the basis of a result of the laser scattering particle size distribution measurement. Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-based material obtained as described above, the pH swing test was performed in the same manner as in Example 1. As a result, after the pH swing process, the silica-based material had a specific surface area of 230 m$^2$/g, a pore volume of 0.27 mL/g and an average pore size of 5.3 nm, which reveals that the structure had not been changed through the pH swing process.

Example 5

Sulfuric acid was added to 10 kg of water glass #3 (SiO$_2$ content: 28 to 30% by mass, Na$_2$O content: 9 to 10% by mass) until pH 9 was attained, and aluminum sulfate was subsequently added thereto to attain pH 2. Then, soda aluminate was further added thereto to attain pH 5 to 5.5, and the resultant solution was partly dehydrated to obtain a hydrogel including approximately 10% by mass of silica-alumina. This hydrogel was spray dried at 130° C. by a spray dryer, and the resultant was washed until it included 0.02% by mass or less of Na$_2$O and 0.5% by mass or less of SO$_4$. To the resultant, 0.83 kg of magnesium oxide and 1.8 kg of nickel oxide were added and the resultant was mixed so as to give a slurry. After filtering and washing, the resultant slurry was dried at 110° C. for 6 hours, was subsequently heated with the temperature increased up to 700° C. over 3 hours and was kept at 700° C. for 3 hours for calcining. Thereafter, the thus obtained substance was slowly cooled to obtain a silica-based material.

The thus obtained silica-based material was found to include 42.2 mol % of silicon, 20.4 mol % of aluminum, 19.8 mol % of nickel and 17.6 mol % of magnesium based on a total mole of silicon, aluminum, nickel and magnesium. The Ni(X)/Al composition ratio was 0.97 on a mole basis and the Ni(X)/Mg(B) composition ratio was 1.13 on a mole basis.

The specific surface area measured by the nitrogen adsorption method was 73 m$^2$/g, the pore volume was 0.26 mL/g and the average pore size was 5.4 nm. The bulk density was 1.05 CBD and the abrasion resistance was 0.1% by mass. The average particle size was found to be 63 μm on the basis of a result of the laser scattering particle size distribution measurement. Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-based material obtained as described above, the pH swing test was performed in the same manner as in Example 1. As a result, after the pH swing process, the silica-based material had a specific surface area of 72 m$^2$/g, a pore volume of 0.27 mL/g and an average pore size of 5.3 nm, which reveals that the structure had not been changed through the pH swing process.

Example 6

A silica-based material including 42.9 mol % of silicon, 37.0 mol % of aluminum, 10.9 mol % of nickel and 9.1 mol % of magnesium was obtained in the same manner as in Example 1 except that 4.4 kg of aluminum oxide was used instead of 1.5 kg of aluminum nitrate nonahydrate, 0.93 kg of nickel oxide was used instead of 0.24 kg of nickel nitrate hexahydrate and 0.42 kg of magnesium oxide was used instead of 0.98 kg of magnesium nitrate hexahydrate and that the calcining temperature was changed from 600° C. to 800° C. The Ni(X)/Al composition ratio was 0.30 on a mole basis and the Ni(X)/Mg(B) composition ratio was 1.20 on a mole basis. The specific surface area measured by the nitrogen adsorption method was 78 $m^2/g$, the pore volume was 0.27 mL/g and the average pore size was 5.2 nm. The bulk density was 1.02 CBD and the abrasion resistance was 0.1%, by mass. The average particle size was found to be 62 μm on the basis of a result of the laser scattering particle size distribution measurement. Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-based material obtained as described above, the pH swing test was performed in the same manner as in Example 1. As a result, after the pH swing process, the silica-based material had a specific surface area of 77 $m^2/g$, a pore volume of 0.27 mL/g and an average pore size of 5.2 nm, which reveals that the structure had not been changed through the pH swing process.

Example 7

A silica-based material including 57.6 mol % of silicon, 3.1 mol % of aluminum, 2.8 mol % of nickel and 36.6 mol % of magnesium was obtained in the same manner as in Example 1 except that 1.0 kg of aluminum nitrate nonahydrate was used instead of 1.5 kg of aluminum nitrate nonahydrate, 0.23 kg of nickel hydroxide was used instead of 0.24 kg of nickel nitrate hexahydrate and 1.9 kg of magnesium hydroxide was used instead of 0.98 kg of magnesium nitrate hexahydrate and that the calcining temperature was changed from 600° C. to 650° C. The Ni(X)/Al composition ratio was 0.91 on a mole basis and the Ni(X)/Mg(B) composition ratio was 0.08 on a mole basis. The specific surface area measured by the nitrogen adsorption method was 92 $m^2/g$, the pore volume was 0.28 mL/g and the average pore size was 5.1 nm. The bulk density was 0.99 CBD and the abrasion resistance was 0.1% by mass. The average particle size was found to be 62 on the basis of a result of the laser scattering particle size distribution measurement. Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-based material obtained as described above, the pH swing test was performed in the same manner as in Example 1. As a result, after the pH swing process, the silica-based material had a specific surface area of 94 $m^2/g$, a pore volume of 0.27 mL/g and an average pore size of 5.0 nm, which reveals that the structure had not been changed through the pH swing process.

Example 8

A hydrothermal treatment was performed by introducing 100 g of the silica-based material, that is, the solid material, obtained in Example 1 into 1.0 L of distilled water heated to 90° C. and keeping the silica-based material therein at 90° C. for 1 hour with stirring.

Subsequently, the mixture resulting from the hydrothermal treatment was allowed to stand still for removing a supernatant, the thus obtained precipitate was washed with distilled water several times and filtered, and the thus obtained solid material was dried at 105° C. for 16 hours. The thus obtained silica-based material had a specific surface area of 240 $m^2/g$, a pore volume of 0.27 mL/g and an average pore size of 3.9 nm. The average particle size of the silica-based material was found to be 62 μm on the basis of a result of the laser scattering particle size distribution measurement. Furthermore, the silica-based material was found to be free from break or crack and be in a substantially spherical shape on the basis of observation with a scanning electron microscope (SEM). An amorphous pattern similar to that of a silica gel was obtained as a result of the powder X-ray diffraction (XRD).

Next, for evaluating the resistance to acids and bases of the silica-based material obtained as described above, the pH swing test was performed in the same manner as in Example 1. As a result, after the pH swing process, the silica-based material had a specific surface area 242 $m^2/g$, a pore volume of 0.26 mL/g and an average pore size of 4.0 nm, which reveals that the structure had not been changed through the pH swing process.

Example 9

An aqueous solution of 2.0 kg of aluminum nitrate nonahydrate, 1.5 kg of magnesium nitrate and 0.27 kg of 60% nitric acid dissolved in 3.0 L of pure water was prepared. The aqueous solution was gradually added dropwise to 10.0 kg of a silica sol solution (trade name "Snowtex N-30" manufactured by Nissan Chemical Industries Ltd., $SiO_2$ content: 30% by mass) kept at 15° C. with stirring and having a colloidal particle size of 10 to 20 nm, so as to give a mixed slurry of a silica sol, aluminum nitrate and magnesium nitrate. Thereafter, the mixed slurry was kept at 50° C. for 24 hours for aging. The aged mixed slurry was cooled to room temperature and was spray dried with a spray dryer with an outlet temperature set to 130° C. to obtain a dried substance.

Subsequently, the obtained dried substance was filled into a thickness of approximately 1 cm within a stainless steel vessel having an open top, and was heated in an electric furnace with a temperature increased from room temperature to 300° C. over 2 hours and kept at 300° C. for 3 hours. The temperature was further increased to 600° C. over 2 hours and was kept at 600° C. for 3 hours for calcining. Thereafter, the resultant substance was slowly cooled, so as to obtain a solid material of silica-alumina-magnesia.

Next, 1.0 L of an aqueous solution including 27 g of nickel nitrate hexahydrate was heated to 90° C. Into this aqueous solution, 300 g of the solid material of silica-alumina-magnesia obtained as described above was introduced, and the resultant solution was kept at 90° C. for 1 hour with stirring, so as to allow a nickel component to deposit on the solid material. Subsequently, the thus obtained mixture was allowed to stand still for removing a supernatant, the resultant precipitate was washed with distilled water several times and filtered, and the thus obtained solid material was dried at 105° C. for 16 hours and then calcined at 600° C. in the air for 5 hours. In this manner, a silica-based material including 80.3 mol % of silicon, 8.7 mol % of aluminum, 1.5 mol % of nickel and 9.5 mol % of magnesium was obtained. The Ni(X)/Al composition ratio was 0.18 on a mole basis and the Ni(X)/Mg(B) composition ratio was 0.16 on a mole basis.

The specific surface area measured by the nitrogen adsorption method was 245 m²/g, the pore volume was 0.26 mL/g and the average pore size was 4.0 nm. The bulk density was 0.99 CBD and the abrasion resistance was 0.1% by mass. The average particle size was found to be 62 μm on the basis of a result of the laser scattering particle size distribution measurement. Furthermore, the silica-based material was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-based material obtained as described above, the pH swing test was performed in the same manner as in Example 1. As a result, after the pH swing process, the silica-based material had a specific surface area of 243 m²/g, a pore volume of 0.27 mL/g and an average pore size of 4.1 nm, which reveals that the structure of the silica-based material had not been changed through the pH swing process.

Example 10

An aqueous solution of 188 g of aluminum nitrate nonahydrate, 145 g of nickel nitrate hexahydrate, 128 g of magnesium nitrate hexahydrate and 46 g of 60% nitric acid dissolved in 552 mL of pure water was prepared. The aqueous solution was gradually added dropwise to 993 g of a silica sol solution (trade name "Snowtex N-30" manufactured by Nissan Chemical Industries Ltd., $SiO_2$ content: 30% by mass) kept at 15° C. with stirring and having a colloidal particle size of 10 to 20 nm, so as to give a mixed slurry of a silica sol, aluminum nitrate, nickel nitrate and magnesium nitrate. Thereafter, the mixed slurry was spray dried with a spray dryer with an outlet temperature set to 130° C. to obtain a solid material.

The solid material was subsequently heated/calcined and slowly cooled in the same manner as in Example 1, whereby obtaining a silica-based material including 76.9 mol % of silicon, 7.7 mol % of aluminum, 7.7 mol % of nickel and 7.7 mol % of magnesium. The Ni(X)/Al composition ratio was 1.0 on a mole basis and the Ni(X)/Mg(B) composition ratio was 1.0 on a mole basis. The specific surface area measured by the nitrogen adsorption method was 130 m²/g, the pore volume was 0.25 mL/g and the average pore size was 7.8 nm. The bulk density was 0.96 CBD and the abrasion resistance was 0.1% by mass. The average particle size was found to be 62 μm on the basis of a result of the laser scattering particle size distribution measurement. Furthermore, the silica-based material was found to be free from break or crack and be in a substantially spherical shape on the basis of observation with a scanning electron microscope (SEM).

Next, for evaluating the resistance to acids and bases of the silica-based material obtained as described above, the pH swing test was performed in the same manner as in Example 1. As a result, after the pH swing process, the silica-based material had a specific surface area of 131 m²/g, a pore volume of 0.26 mL/g and an average pore size of 7.9 nm, which reveals that the structure of the silica-based material had been minimally changed through the pH swing process.

Example 11

A silica-based material including 74.1 mol % of silicon, 7.4 mol % of aluminum, 11.1 mol % of nickel and 7.4 mol % of magnesium was obtained in the same manner as in Example 10 except that 218 g of nickel nitrate was used instead of 145 g of nickel nitrate hexahydrate and 704 mL of pure water was used instead of 552 mL of pure water. The Ni(X)/Al composition ratio was 1.5 on a mole basis and the Ni(X)/Mg(B) composition ratio was 1.5 on a mole basis. The specific surface area measured by the nitrogen adsorption method was 100 m²/g, the pore volume was 0.20 mL/g and the average pore size was 8.2 nm. The bulk density was 0.95 CBD and the abrasion resistance was 0.1% by mass. The average particle size was found to be 63 μm on the basis of a result of the laser scattering particle size distribution measurement. Furthermore, the silica-based material was found to be free from break or crack and be in a substantially spherical shape on the basis of observation with a scanning electron microscope (SEM).

Next, for evaluating the resistance to acids and bases of the silica-based material obtained as described above, the pH swing test was performed in the same manner as in Example 1. As a result, after the pH swing process, the silica-based material had a specific surface area of 99 m²/g, a pore volume of 0.20 mL/g and an average pore size of 8.3 nm, which reveals that the structure of the silica-based material had been minimally changed through the pH swing process.

Example 12

To 100 mL of distilled water contained in a glass vessel, 30 g of the silica-based material obtained in Example 9 was added, a prescribed amount of a palladium chloride aqueous solution was further added dropwise thereto with stirring at 60° C., and a 0.5 N sodium hydroxide aqueous solution was further added thereto for adjusting the aqueous solution to pH 8. After successively stirring the thus obtained mixed liquid for further 1 hour, the mixed liquid was allowed to stand still for removing a supernatant, the thus obtained precipitate was washed with distilled water until no Cl ions were detected and the thus obtained solid material was dried at 105° C. for 16 hours and then calcined in the air at 300° C. for 5 hours. Subsequently, the resultant solid material was subjected to a reduction treatment in a hydrogen atmosphere at 400° C. for 3 hours, whereby obtaining a noble metal-supported material supporting 2.4% by mass of palladium.

As for the noble metal-supported material, the specific surface area measured by the nitrogen adsorption method was 247 m²/g, the pore volume was 0.26 mL/g and the average pore size was 4.0 nm. The average particle size of the obtained noble metal-supported material was found to be 62 μm on the basis of a result of the laser scattering particle size distribution measurement. Furthermore, the noble metal-supported material was found to be free from break or crack and be in a substantially spherical shape on the basis of observation with a scanning electron microscope (SEM).

The form of the noble metal-supported material was observed with a transmission electron microscope (TEM), resulting in finding that palladium particles having a maximum distribution in a particle size of 4 to 5 nm (number average particle size: 4.3 nm (calculated based on 100 particles)) were supported on the silica-based material working as the support.

Next, for evaluating the resistance to acids and bases of the noble metal-supported material obtained as described above, the pH swing test was performed in the same manner as in Example 1. As a result, after the pH swing process, the noble metal-supported material had a specific surface area of 245 m²/g, a pore volume of 0.26 mL/g and an average pore size of 4.1 nm, which reveals that the structure had not been changed through the pH swing process. Furthermore, the average particle size of the palladium particles obtained with a transmission electron microscope (TEM) was 4.4 nm (calculated based on 100 particles) and sintering of the palladium particles was minimally observed.

Example 13

To 100 mL of distilled water contained in a glass vessel, 30 g of the silica-based material obtained in Example 4 was added, a prescribed amount of a ruthenium chloride aqueous solution was further added dropwise thereto with stirring at 80° C., and a 0.5 N sodium hydroxide aqueous solution was further added thereto for adjusting the aqueous solution to pH 8. After successively stirring the thus obtained mixed liquid for further 1 hour, the mixed liquid was allowed to stand still for removing a supernatant, the thus obtained precipitate was washed with distilled water until no Cl ions were detected and the thus obtained solid material was dried at 105° C. for 16 hours and then calcined in the air at 300° C. for 3 hours. Subsequently, the resultant solid material was subjected to a reduction treatment in a hydrogen atmosphere at 350° C. for 3 hours, whereby obtaining a noble metal-supported material supporting 2.1% by mass of ruthenium.

As for the noble metal-supported material, the specific surface area measured by the nitrogen adsorption method was 241 m²/g, the pore volume was 0.27 mL/g and the average pore size was 3.9 nm. The average particle size of the obtained noble metal-supported material was found to be 62 µm on the basis of a result of the laser scattering particle size distribution measurement. Furthermore, the noble metal-supported material was found to be free from break or crack and be in a substantially spherical shape on the basis of observation with a scanning electron microscope (SEM).

The form of the noble metal-supported material was observed with a transmission electron microscope (TEM), resulting in finding that ruthenium particles having a maximum distribution in a particle size of 4 to 5 nm (number average particle size: 4.4 nm (calculated based on 100 particles)) were supported on the silica-based material working as the support.

Next, for evaluating the resistance to acids and bases of the noble metal-supported material obtained as described above, the pH swing test was performed in the same manner as in Example 1. As a result, after the pH swing process, the noble metal-supported material had a specific surface area of 240 m²/g, a pore volume of 0.26 mL/g and an average pore size of 4.2 nm, which reveals that the structure had not been changed through the pH swing process. Furthermore, the average particle size of the ruthenium particles obtained with a transmission electron microscope (TEM) was 4.7 nm (calculated based on 100 particles) and sintering of the ruthenium particles was minimally observed.

Example 14

To 100 mL of distilled water contained in a glass vessel, 30 g of the silica-based material obtained in Example 2 was added, a prescribed amount of a chloroauric acid aqueous solution was further added dropwise thereto with stirring at 80° C., and a 0.5 N sodium hydroxide aqueous solution was further added thereto for adjusting the aqueous solution to pH 8. After successively stirring the thus obtained mixed liquid for further 1 hour, the mixed liquid was allowed to stand still for removing a supernatant, the thus obtained precipitate was washed with distilled water until no Cl ions were detected and the thus obtained solid material was dried at 105° C. for 16 hours and then calcined in the air at 400° C. for 3 hours, whereby obtaining a noble metal-supported material supporting 1.8% by mass of gold.

As for the noble metal-supported material, the specific surface area measured by the nitrogen adsorption method was 175 m²/g, the pore volume was 0.27 mL/g and the average pore size was 4.0 nm. The average particle size of the obtained noble metal-supported material was found to be 62 µm on the basis of a result of the laser scattering particle size distribution measurement. Furthermore, the noble metal-supported material was found to be free from break or crack and be in a substantially spherical shape on the basis of observation with a scanning electron microscope (SEM).

The form of the noble metal-supported material was observed with a transmission electron microscope (TEM), resulting in finding that gold particles having a maximum distribution in a particle size of 3 to 4 nm (number average particle size: 3.5 nm (calculated based on 100 particles)) were supported on the silica-based material working as the support.

Next, for evaluating the resistance to acids and bases of the noble metal-supported material obtained as described above, the pH swing test was performed in the same manner as in Example 1. As a result, after the pH swing process, the noble metal-supported material had a specific surface area of 173 m²/g, a pore volume of 0.26 mL/g and an average pore size of 4.5 nm, which reveals that the structure had been minimally changed through the pH swing process. Furthermore, the average particle size of the gold particles obtained with a transmission electron microscope (TEM) was 3.9 nm (calculated based on 100 particles) and sintering of the gold particles was minimally observed.

The physical properties of the silica-based materials of Examples 1 to 11 and the noble metal-supported materials of Examples 12 to 14 are shown in Table 1.

TABLE 1

| Example | Composition (mol %) | | | | | | X/A | X/B | Specific Surface Area (m²/g) | Pore Volume (mL/g) | Pore Size (nm) |
| | X | Base (B) | Si | Al | X | Base (B) | | | | | |
| --- | --- | --- | --- | --- | --- | --- | --- | --- | --- | --- | --- |
| 1 | Ni | Mg | 85.3 | 6.8 | 1.4 | 6.5 | 0.21 | 0.22 | 223 | 0.26 | 5.1 |
| 2 | Zn | K | 69.7 | 15.0 | 0.5 | 14.9 | 0.03 | 0.03 | 170 | 0.27 | 5.3 |
| 3 | Co | Rb | 82.7 | 8.8 | 43 | 43 | 0.49 | 0.99 | 196 | 0.26 | 5.1 |
| 4 | Fe | La | 89.9 | 7.2 | 0.9 | 2.0 | 0.12 | 0.45 | 232 | 0.28 | 5.0 |
| 5 | Ni | Mg | 42.2 | 20.4 | 19.8 | 17.6 | 0.97 | 1.13 | 73 | 0.26 | 5.4 |
| 6 | Ni | Mg | 42.9 | 37.0 | 10.9 | 9.1 | 0.30 | 1.20 | 78 | 0.27 | 5.2 |
| 7 | Ni | Mg | 57.6 | 3.1 | 2.8 | 36.6 | 0.91 | 0.08 | 92 | 0.28 | 5.1 |
| 8 | Ni | Mg | 85.3 | 6.8 | 1.4 | 6.5 | 0.21 | 0.22 | 240 | 0.27 | 3.9 |
| 9 | Ni | Mg | 80.3 | 8.7 | 1.5 | 9.5 | 0.18 | 0.16 | 245 | 0.26 | 4.0 |
| 10 | Ni | Mg | 76.9 | 7.7 | 7.7 | 7.7 | 1.0 | 1.0 | 130 | 0.25 | 7.8 |
| 11 | Ni | Mg | 74.1 | 7.4 | 11.1 | 7.4 | 1.5 | 1.5 | 100 | 0.20 | 8.2 |

TABLE 1-continued

| Example | X | Base (B) | Si | Al | X | Base (B) | X/A | X/B | Specific Surface Area (m²/g) | Pore Volume (mL/g) | Pore Size (nm) |
|---------|----|----|------|------|-----|------|------|------|-----|------|-----|
| 12 | Ni | Mg | 80.3 | 8.7 | 1.5 | 9.5 | 0.18 | 0.16 | 247 | 0.26 | 4.0 |
| 13 | Fe | La | 89.9 | 7.2 | 0.9 | 2.0 | 0.12 | 0.45 | 241 | 0.27 | 3.9 |
| 14 | Zn | K | 69.7 | 15.0 | 0.5 | 14.9 | 0.03 | 0.03 | 175 | 0.27 | 4.0 |

Comparative Example 1

A solid material was obtained in the same manner as in Example 1 by performing procedures up to the spray drying of the mixed slurry with a spray dryer except that the silica sol solution used as a raw material with the trade name of the "Snowtex N-30" manufactured by Nissan Chemical Industries, Ltd. was replaced with one having a trade name "Snowtex N-40" ($SiO_2$ content: 40% by mass) manufactured by the same firm and that a composition including silica alone and including none of aluminum nitrate, nickel nitrate and magnesium nitrate was employed. Next, the obtained solid material was heated in a rotary kiln with a temperature increased from room temperature to 300° C. over 2 hours and kept at 300° C. for 1 hour. After further increasing the temperature to 600° C. over 2 hours, the solid material was kept at 600° C. for 1 hour for calcining. Thereafter, the resultant solid material was slowly cooled to obtain silica.

The specific surface area measured by the nitrogen adsorption method was 215 m²/g, the pore volume was 0.26 mL/g and the average pore size was 5.5 nm. The bulk density was 0.55 CBD and the abrasion resistance was 3.3% by mass. The average particle size was found to be 66 μm on the basis of a result of the laser scattering particle size distribution measurement. Furthermore, the silica was found to have some break or crack on the basis of observation with a scanning electron microscope (SEM). The silica was in a substantially spherical shape. As for the form of the solid material, an amorphous pattern was obtained as a result of the powder X-ray diffraction (XRD).

Next, for evaluating the resistance to acids and bases of the silica obtained as described above, the pH swing test was performed in the same manner as in Example 1. As a result, after the pH swing process, the silica had a specific surface area of 198 m²/g, a pore volume of 0.27 mL/g and an average pore size of 9.8 nm, which reveals that the structure had been changed through the pH swing process.

Comparative Example 2

A silica-alumina composition including 93.0 mol % of silicon and 7.0 mol % of aluminum was obtained in the same manner as in Example 1 except that none of nickel nitrate and magnesium nitrate was used. The specific surface area measured by the nitrogen adsorption method was 220 m²/g, the pore volume was 0.30 mL/g and the average pore size was 5.2 nm. The bulk density was 0.94 CBD and the abrasion resistance was 0.2% by mass. The average particle size of the silica-alumina composition was found to be 62 μm on the basis of a result of the laser scattering particle size distribution measurement. Furthermore, the silica-alumina composition was found to be free from break or crack and be in a substantially spherical shape on the basis of observation with a scanning electron microscope (SEM). As for the form of the solid material, an amorphous pattern was obtained as a result of the powder X-ray diffraction (XRD).

Next, for evaluating the resistance to acids and bases of the silica-alumina composition obtained as described above, the pH swing test was performed in the same manner as in Example 1. As a result, after the pH swing process, the silica-based material had a specific surface area of 210 m²/g, a pore volume of 0.32 mL/g and an average pore size of 9.5 nm, which reveals that the structure had been changed through the pH swing process.

Comparative Example 3

A silica-alumina-magnesia composition including 86.5 mol % of silicon, 6.9 mol % of aluminum and 6.6 mol % of magnesium was obtained in the same manner as in Example 1 except that no nickel nitrate was used. The specific surface area measured by the nitrogen adsorption method was 213 m²/g, the pore volume was 0.27 mL/g and the average pore size was 5.1 nm. The bulk density was 0.96 CBD and the abrasion resistance was 0.1% by mass. The average particle size of the silica-alumina-magnesia composition was found to be 62 μm on the basis of a result of the laser scattering particle size distribution measurement. Furthermore, the silica-alumina-magnesia composition was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-alumina-magnesia composition obtained as described above, the pH swing test was performed in the same manner as in Example 1. As a result, after the pH swing process, the silica-alumina-magnesia had a specific surface area of 204 m²/g, a pore volume of 0.26 mL/g and an average pore size of 8.5 nm, which reveals that the structure had been changed through the pH swing process.

Comparative Example 4

A silica-alumina-nickel oxide-magnesia composition including 37.3 mol % of silicon, 46.2 mol % of aluminum, 10.1 mol % of nickel and 6.5 mol % of magnesium was obtained in the same manner as in Example 1 except that 2.3 kg of aluminum nitrate nonahydrate was used instead of 1.5 kg of aluminum nitrate nonahydrate, 0.37 kg of nickel nitrate hexahydrate was used instead of 0.24 kg of nickel nitrate hexahydrate, 0.21 kg of magnesium nitrate hexahydrate was used instead of 0.98 kg of magnesium nitrate hexahydrate and 10.0 kg of the silica sol solution (manufactured by Nissan Chemical Industries Ltd., trade name "Snowtex N-30", $SiO_2$ content: 30% by mass) was replaced with 1.0 kg of the same silica sol solution. The Ni(X)/Al composition ratio was 0.22 on a mole basis and the Ni(X)/Mg(B) composition ratio was 1.56 on a mole basis. The specific surface area measured by the nitrogen adsorption method was 195 m$^2$/g, the pore volume was 0.3 mL/g and the average pore size was 5.3 nm. The bulk density was 0.85 CBD and the abrasion resistance was 0.5% by mass. The average particle size was found to be 64 µm on the basis of a result of the laser scattering particle size distribution measurement. Furthermore, the silica-alumina-nickel oxide-magnesia composition was found to have some break or crack on the basis of observation with a scanning electron microscope (SEM). The shape was substantially spherical. As for the form of the solid material, a crystal pattern derived from alumina was obtained as a result of the powder X-ray diffraction (XRD).

Next, for evaluating the resistance to acids and bases of the silica-alumina-nickel oxide-magnesia composition obtained as described above, the pH swing test was performed in the same manner as in Example 1. As a result, after the pH swing process, the silica-alumina-nickel oxide-magnesia composition had a specific surface area of 180 m$^2$/g, a pore volume of 0.29 mL/g and an average pore size of 8.7 nm, which reveals that the structure had been changed through the pH swing process.

Comparative Example 5

A silica-alumina-nickel oxide-magnesia composition including 93.1 mol % of silicon, 5.0 mol % of aluminum, 0.3 mol % of nickel and 1.6 mol % of magnesium was obtained in the same manner as in Example 1 except that 1.0 kg of aluminum nitrate nonahydrate was used instead of 1.5 kg of aluminum nitrate nonahydrate, 0.05 kg of nickel nitrate hexahydrate was used instead of 0.24 kg of nickel nitrate hexahydrate, and 0.23 kg of magnesium nitrate hexahydrate was used instead of 0.98 kg of magnesium nitrate hexahydrate. The Ni(X)/Al composition ratio was 0.07 on a mole basis and the Ni(X)/Mg(B) composition ratio was 0.22 on a mole basis. The specific surface area measured by the nitrogen adsorption method was 210 m$^2$/g, the pore volume was 0.27 mL/g and the average pore size was 5.4 nm. The bulk density was 0.9 CBD and the abrasion resistance was 2.0% by mass. The average particle size was found to be 65 µm on the basis of a result of the laser scattering particle size distribution measurement. Furthermore, the silica-alumina-nickel oxide-magnesia composition was found to have some break or crack on the basis of observation with a scanning electron microscope (SEM). The shape was substantially spherical. As for the form of the solid material, an amorphous pattern similar to that of a silica gel was obtained as a result of the powder X-ray diffraction (XRD).

Next, for evaluating the resistance to acids and bases of the silica-alumina-nickel oxide-magnesia composition obtained as described above, the pH swing test was performed in the same manner as in Example 1. As a result, after the pH swing process, the silica-alumina-nickel oxide-magnesia composition had a specific surface area of 195 m$^2$/g, a pore volume of 0.27 mL/g and an average pore size of 8.5 nm, which reveals that the structure had been changed through the pH swing process.

Comparative Example 6

A silica-alumina-manganese oxide-magnesia composition including 85.3 mol % of silicon, 6.8 mol % of aluminum, 1.4 mol % of manganese and 6.5 mol % of magnesium was obtained in the same manner as in Example 1 except that 0.24 kg of manganese nitrate hexahydrate was used instead of 0.24 kg of nickel nitrate hexahydrate. The specific surface area measured by the nitrogen adsorption method was 220 m$^2$/g, the pore volume was 0.27 mL/g and the average pore size was 5.1 nm. The bulk density was 0.98 CBD and the abrasion resistance was 0.1% by mass. The average particle size was found to be 62 µm on the basis of a result of the laser scattering particle size distribution measurement. Furthermore, the shape was found to be substantially spherical on the basis of observation with a scanning electron microscope (SEM). As for the form of the solid material, an amorphous pattern similar to that of a silica gel was obtained as a result of the powder X-ray diffraction (XRD).

Next, for evaluating the resistance to acids and bases of the silica-alumina-manganese oxide-magnesia composition obtained as described above, the pH swing test was performed in the same manner as in Example 1. As a result, after the pH swing process, the silica-alumina-manganese oxide-magnesia composition had a specific surface area of 210 m$^2$/g, a pore volume of 0.27 mL/g and an average pore size of 8.1 nm, which reveals that the structure had been changed through the pH swing process.

Comparative Example 7

A noble metal-supported material in which palladium was supported on a silica-alumina-magnesia composition was obtained in the same manner as in Example 12 except that no nickel nitrate was used. The thus obtained noble metal-supported material was found to include 81.7 mol % of silicon, 8.8 mol % of aluminum and 9.5 mol % of magnesium based on a total mole of silicon, aluminum and magnesium. The amount of palladium supported therein was 2.1% by mass.

The specific surface area measured by the nitrogen adsorption method was 243 m$^2$/g, the pore volume was 0.27 mL/g and the average pore size was 4.1 nm. The average particle size of the noble metal-supported material was found to be 62 µm on the basis of a result of the laser scattering particle size distribution measurement. Furthermore, the noble metal-supported material was found to be free from break or crack and be in a substantially spherical shape on the basis of observation with a scanning electron microscope (SEM).

The form of the noble metal-supported material was observed with a transmission electron microscope (TEM), resulting in finding that palladium particles having a maximum distribution in a particle size of 4 to 5 nm (number average particle size: 4.2 nm (calculated based on 100 particles)) were supported on the support.

Next, for evaluating the resistance to acids and bases of the noble metal-supported material obtained as described above, the pH swing test was performed in the same manner as in Example 1. As a result, after the pH swing process, the noble metal-supported material had a specific surface area of 224 m$^2$/g, a pore volume of 0.28 mL/g and an average pore size of 8.4 nm, which reveals that the structure had been changed through the pH swing process. Furthermore, the average particle size of the complex particles obtained with a transmission electron microscope (TEM) was 6.7 nm (calculated based on 100 particles) and not only increase of the pore size of the noble metal-supported material but also sintering of the palladium particles was observed.

Example 15

To 1 L of distilled water contained in a glass vessel, 300 g of the silica-based material obtained in Example 1 was added, and a prescribed amount of a chloroauric acid aqueous solution was rapidly added dropwise thereto with stirring at 60° C. Subsequently, a 0.5 N sodium hydroxide aqueous solution was further added thereto for adjusting the aqueous solution to pH 8 and the solution was successively stirred for further 1 hour. Thereafter, the glass vessel was allowed to stand still for removing a supernatant to collect a precipitate, the precipitate was washed with distilled water until no Cl ions were detected and the washed substance was dried at 105° C. for 16 hours and then calcined in the air at 400° C. for 5 hours, whereby obtaining a noble metal-supported material supporting 2.0% by mass of Au (a 2% Au/Si—Al—Ni—Mg composite oxide).

As for the noble metal-supported material, the specific surface area measured by the nitrogen adsorption method was 242 $m^2/g$, the pore volume was 0.27 mL/g and the average pore size was 3.9 nm. The average particle size was found to be 62 μm on the basis of a result of the laser scattering particle size distribution measurement. Furthermore, the noble metal-supported material was found to be free from break or crack and be in a substantially spherical shape on the basis of observation with a scanning electron microscope (SEM).

According to a result of the powder X-ray diffraction (XRD) of the noble metal-supported material, a diffraction peak derived from Au was observed. The fine structure of the noble metal-supported material was observed with a transmission electron microscope (TEM), resulting in finding that Au particles having a particle size of 2 to 3 nm were uniformly supported on the surface of the support. The Au particles had a number average particle size of 3.1 nm (calculated based on 100 particles).

Next, for evaluating the resistance to acids and bases of the noble metal-supported material, the pH swing test was performed in the same manner as in Example 1. As a result, after the pH swing process, the noble metal-supported material had a specific surface area of 243 $m^2/g$, a pore volume of 0.27 mL/g and an average pore size of 3.9 nm, which reveals that the structure of the noble metal-supported material had not been changed through the pH swing process. Furthermore, the average particle size of the Au particles obtained with a transmission electron microscope (TEM/STEM) was 3.2 nm (calculated based on 100 particles) and sintering of the Au particles was minimally observed.

As a catalyst, 240 g of the noble metal-supported material (the 2% Au/Si—Al—Ni—Mg composite oxide) was charged in a stainless steel stirring reactor equipped with a catalyst separator and having a liquid phase part of 1.2 liters. While stirring the content at a rate at a tip speed of stirring blade of the reactor of 4 m/sec., an oxidative production reaction of carboxylic acid ester from aldehyde and alcohol was carried out. A 36.7% by mass methacrolein/methanol solution and a 1 to 4% by mass NaOH/methanol solution were continuously supplied to the reactor respectively at 0.6 lit/h and at 0.06 lit/h. The air was blown in at a reaction temperature of 80° C. and a reaction pressure of 0.5 MPa so that an outlet oxygen concentration could be 4.0 vol % (corresponding to an oxygen partial pressure of 0.02 MPa), and the concentration of NaOH supplied to the reactor was adjusted so that the pH of the reaction system became 7. The obtained reaction product was continuously extracted by an overflow line from an outlet of the reactor, and its composition was analyzed through gas chromatography for examining reactivity.

In measurement performed 500 hours after the start of the reaction, a degree of conversion of methacrolein was 45.8%, selectivity of methyl methacrylate was 87.5%, and activity for producing methyl methacrylate per unit mass of the catalyst was 4.36 mol/h/kg-cat. In measurement performed 1000 hours after the start of the reaction, a degree of conversion of methacrolein was 45.5%, selectivity of methyl methacrylate was 87.4%, and activity for producing methyl methacrylate was 4.33 mol/h/kg-cat, and the reaction activity was minimally changed.

The catalyst was extracted, 1000 hours after the start of the reaction, to be examined with a scanning electron microscope (SEM), resulting in finding that break or crack was minimally caused in the catalyst particles. Furthermore, the catalyst had a specific surface area measured by the nitrogen adsorption method of 243 $m^2/g$, a pore volume of 0.27 mL/g and an average pore size of 4.0 nm.

Next, the catalyst extracted 1000 hours after the start of the reaction was observed with a transmission electron microscope (TEM/STEM), resulting in finding that nanoparticles having a maximum distribution in a particle size of 2 to 3 nm (number average particle size: 3.3 nm) were supported on the support, and no sintering of the Au particles was observed.

Example 16

To 1 L of distilled water contained in a glass vessel, 300 g of the support obtained in Example 1 was added, and a dilute hydrochloric acid of palladium chloride and a lead nitrate aqueous solution respectively in amounts corresponding to 2.5% by mass of Pd and Pb were rapidly added dropwise thereto with stirring at 60° C. Subsequently, the content of the glass vessel was allowed to be stirring for 1 hour, and hydrazine in an amount 1.2 times as large as a stoichiometric amount was added thereto for reduction. A supernatant was removed by decantation from the content resulting from the reduction to collect a precipitate, the precipitate was washed with distilled water until no Cl ions were detected and the washed substance was dried at 60° C. in a vacuum, whereby obtaining a noble metal-supported material supporting 2.5% by mass of Pd and 2.5% by mass of Pb (a PdPb/Si—Al—Ni—Mg composite oxide).

As for the noble metal-supported material, the specific surface area measured by the nitrogen adsorption method was 240 $m^2/g$, the pore volume was 0.26 mL/g and the average pore size was 4.0 nm. The average particle size was found to be 62 μm on the basis of a result of the laser scattering particle size distribution measurement. Furthermore, the noble metal-supported material was found to be free from break or crack and be in a substantially spherical shape on the basis of observation with a scanning electron microscope (SEM).

According to a result of the powder X-ray diffraction (XRD) of the noble metal-supported material, a diffraction peak (2θ=38.6°, 44.8°, 65.4°, 78.6°) derived from an intermetallic compound of $Pd_3Pb_1$ was observed. The fine structure of the noble metal-supported material was observed with a transmission electron microscope (TEM), resulting in finding that PdPb particles having a particle size of 5 to 6 nm were uniformly supported on the surface of the support. The PdPb particles had a number average particle size of 5.5 nm (calculated based on 100 particles).

Next, for evaluating the chemical stability of the noble metal-supported material obtained as described above, the pH swing test was performed in the same manner as in Example 1. As a result, after the pH swing process, the noble metal-supported material had a specific surface area of 241 $m^2/g$, a pore volume of 0.27 mL/g and an average pore size of 4.0 nm, which reveals that the structure had not been changed through the pH swing process. Furthermore, the average particle size of the PdPb particles obtained with a transmission electron microscope (TEM) was 5.1 nm (calculated based on 100 particles) and particle growth of the PdPb particles was minimally observed.

Methyl methacrylate was produced from methacrolein in the same manner as in Example 15 except that 240 g of the noble metal-supported material (the PdPb/Si—Al—Ni—Mg composite oxide) obtained as described above was used as a catalyst.

In measurement performed 500 hours after the start of the reaction, a degree of conversion of methacrolein was 44.2%, selectivity of methyl methacrylate was 91.5%, and activity for producing methyl methacrylate per unit mass of the catalyst was 4.40 mol/h/kg-cat. In measurement performed 1000 hours after the start of the reaction, a degree of conversion of methacrolein was 44.6%, selectivity of methyl methacrylate was 91.3%, and activity for producing methyl methacrylate was 4.43 mol/h/kg-cat, and the reaction activity was minimally changed.

The catalyst was extracted, 1000 hours after the start of the reaction, to be examined with a scanning electron microscope (SEM), resulting in finding that break or crack was minimally caused in the catalyst particles. Furthermore, the catalyst had a specific surface area measured by the nitrogen adsorption method of 241 $m^2/g$, a pore volume of 0.27 mL/g and an average pore size of 4.1 nm.

Next, the catalyst extracted 1000 hours after the start of the reaction was observed with a transmission electron microscope (TEM/STEM), resulting in finding that nanoparticles having a maximum distribution in a particle size of 5 to 6 nm (number average particle size: 5.2 nm) were supported on the support, and no sintering of the PdPb particles was observed.

Example 17

Methyl methacrylate was produced from methacrolein in the same manner as in Example 15 except that 240 g of the noble metal-supported material obtained in Example 14 (the Au/Si—Al—Zn—K composite oxide) was used as a catalyst.

In measurement performed 500 hours after the start of the reaction, a degree of conversion of methacrolein was 33.5%, selectivity of methyl methacrylate was 86.7%, and activity for producing methyl methacrylate per unit mass of the catalyst was 3.16 mol/h/kg-cat. In measurement performed 1000 hours after the start of the reaction, a degree of conversion of methacrolein was 33.2%, selectivity of methyl methacrylate was 86.5%, and activity for producing methyl methacrylate was 3.12 mol/h/kg-cat, and the reaction activity was minimally changed.

The catalyst was extracted, 1000 hours after the start of the reaction, to be examined with a scanning electron microscope (SEM), resulting in finding that break or crack was minimally caused in the catalyst particles. Furthermore, the catalyst had a specific surface area measured by the nitrogen adsorption method of 171 $m^2/g$, a pore volume of 0.26 mL/g and an average pore size of 4.7 nm.

Next, the catalyst extracted 1000 hours after the start of the reaction was observed with a transmission electron microscope (TEM/STEM), resulting in finding that nanoparticles having a maximum distribution in a particle size of 3 to 4 nm (number average particle size: 4.1 nm) were supported on the support, and sintering of the Au particles was minimally observed.

Comparative Example 8

A noble metal-supported material supporting 2.0% by mass of Au (2% Au/SiO$_2$—Al$_2$O$_3$—MgO) was obtained in the same manner as in Example 15 except that the silica-based material obtained in Comparative Example 3 was used as a support.

As for the noble metal-supported material, the specific surface area measured by the nitrogen adsorption method was 232 $m^2/g$, the pore volume was 0.28 mL/g and the average pore size was 4.0 nm. The average particle size was found to be 62 μm on the basis of a result of the laser scattering particle size distribution measurement. Furthermore, the noble metal-supported material was found to be free from break or crack and be in a substantially spherical shape on the basis of observation with a scanning electron microscope (SEM).

The fine structure of the noble metal-supported material was observed with a transmission electron microscope (TEM), resulting in finding that Au particles having a particle size of 3 to 4 nm were uniformly supported on the surface of the support. The Au particles had a number average particle size of 3.4 nm (calculated based on 100 particles).

Next, for evaluating the resistance to acids and bases of the noble metal-supported material, the pH swing test was performed in the same manner as in Example 1. As a result, after the pH swing process, the noble metal-supported material had a specific surface area of 242 $m^2/g$, a pore volume of 0.27 mL/g and an average pore size of 8.2 nm, which reveals that the structure had been changed through the pH swing process. Furthermore, the average particle size of the Au particles obtained with a transmission electron microscope (TEM) was 5.6 nm (calculated based on 100 particles) and the particle growth of the Au particles was observed.

The reaction was conducted in the same manner as in Example 15 except that the noble metal-supported material (2% Au/SiO$_2$—Al$_2$O$_3$—MgO) was used. As a result, in measurement performed 500 hours after the start of the reaction, a degree of conversion of methacrolein was 39.4%, selectivity of methyl methacrylate was 82.1%, and activity for producing methyl methacrylate per unit mass of the catalyst was 3.52 mol/h/kg-cat. In measurement performed 1000 hours after the start of the reaction, a degree of conversion of methacrolein was 31.1%, selectivity of methyl methacrylate was 78.2%, and activity for producing methyl methacrylate was 2.39 mol/h/kg-cat, and the reaction activity was found to be lowered.

The catalyst was extracted, 1000 hours after the start of the reaction, to be examined with a scanning electron microscope (SEM), resulting in finding that break or crack was minimally caused in the catalyst particles. Furthermore, the catalyst had a specific surface area measured by the nitrogen adsorption method of 212 $m^2/g$, a pore volume of 0.27 mL/g and an average pore size of 8.2 nm, and thus, the structure of the catalyst was found to have been changed.

Next, the catalyst extracted 1000 hours after the start of the reaction was observed with a transmission electron microscope (TEM), resulting in finding that the Au particles had a number average particle size of 5.5 nm, and not only increase of the pore size but also sintering of the Au particles was observed.

Example 18

A high-pressure autoclave-type reactor (total volume: 120 ml) made of SUS316 stainless steel equipped with a magnetic stirrer was charged with 0.5 g of the same noble metal-supported material (2% Au/Si—Al—Ni—Mg composite oxide) as that of Example 15, 0.5 g of methacrolein, 6.3 g of water and 3.2 g of acetonitrile serving as a solvent, the autoclave was closed, an atmosphere in a system was replaced with a nitrogen gas, and thereafter, a mixed gas of nitrogen including 7 vol % of oxygen was introduced into a gas phase part, whereby increasing the total pressure within the system up to 3.0 MPa.

Subsequently, the reactor was fixed in an oil bath, and a reaction was conducted for 4 hours with stirring at a reaction temperature of 100° C. After cooling, a residual pressure was removed and the autoclave was opened, the catalyst was filtered out, and a filtrate was analyzed by the gas chromatography. As a result, a degree of conversion of methacrolein was 49.7%, methacrylic acid selectivity was 95.3%, and a yield of methacrylic acid was 47.4%.

Example 19

Methacrylic acid was produced from methacrolein by using the same noble metal-supported material (2% Au/Si—Al—Ni—Mg composite oxide) as that of Example 15 in the same manner as in Example 18 except that acetone was used as a solvent. As a result, a degree of conversion of methacrolein was 61.1%, methacrylic acid selectivity was 96.6% and a yield of methacrylic acid was 59.0%.

Examples 20

Methacrylic acid was produced from methacrolein by using the same noble metal-supported material (2% Au/Si—Al—Ni—Mg composite oxide) as that of Example 15 in the same manner as in Example 18 except that tertiary butanol was used as a solvent. As a result, a degree of conversion of methacrolein was 64.7%, methacrylic acid selectivity was 96.8% and a yield of methacrylic acid was 62.6%.

Example 21

1.0 L of an aqueous solution including prescribed amounts of a chloroauric acid aqueous solution and nickel nitrate hexahydrate was heated to 90° C. Into this aqueous solution, 300 g of the silica-based material obtained in Example 1 was introduced, and the resultant mixed liquid was stirred for 1 hour with the temperature kept at 90° C., so as to cause a gold component and a nickel component deposit on the silica-based material.

Subsequently, the solution was allowed to stand still for removing a supernatant, the thus obtained precipitate was washed with distilled water several times and filtered. The resultant was dried at 105° C. for 16 hours and then calcined in the air at 500° C. for 3 hours, whereby obtaining a noble metal-supported material carrying 1.5% by mass of gold and 1.5% by mass of nickel (an AuNiO/Si—Al—Ni—Mg composite oxide).

As for the noble metal-supported material, the specific surface area measured by the nitrogen adsorption method was 227 m$^2$/g, the pore volume was 0.26 mL/g and the average pore size was 4.9 nm. The average particle size was found to be 65 µm on the basis of a result of the laser scattering particle size distribution measurement. Furthermore, the noble metal-supported material was found to be free from break or crack and be in a substantially spherical shape on the basis of observation with a scanning electron microscope (SEM).

The fine structure of the noble metal-supported material was observed with a transmission electron microscope (TEM), resulting in finding that metal particles having a particle size of 2 to 3 nm were uniformly supported on the surface of the silica-based material. The metal particles had a number average particle size of 3.0 nm (calculated based on 100 particles).

Next, for evaluating the chemical stability of the noble metal-supported material obtained as described above, the pH swing test was performed in the same manner as in Example 1. As a result, after the pH swing process, the noble metal-supported material had a specific surface area of 229 m$^2$/g, a pore volume of 0.27 mL/g and an average pore size of 4.9 nm, which reveals that the structure had not been changed through the pH swing process. Furthermore, the average particle size of the metal particles obtained with a transmission electron microscope (TEM) was 3.0 nm (calculated based on 100 particles) and particle growth of the metal particles was minimally observed.

Methacrylic acid was produced from methacrolein by using the noble metal-supported material (the AuNiO/Si—Al—Ni—Mg composite oxide) in the same manner as in Example 16. As a result, a degree of conversion of methacrolein was 59.9%, methacrylic acid selectivity was 96.1% and a yield of methacrylic acid was 57.6%.

Example 22

A stirring type autoclave (15 L) made of SUS316 stainless steel was charged with 50 g of the same noble metal-supported material (the AuNiO/Si—Al—Ni—Mg composite oxide) as that of Example 21, 100 g of methacrolein, 580 g of water and 320 g of acetone serving as a solvent, the autoclave was closed, an atmosphere in a system was replaced with a nitrogen gas, and thereafter, a mixed gas of nitrogen including 7 vol % of oxygen was introduced into a gas phase part, whereby increasing the total pressure within the system up to 3.0 MPa.

After conducting a reaction for 8 hours at a reaction temperature of 110° C., the autoclave was cooled, a residual pressure was removed and the autoclave was opened, and the thus obtained reaction solution was analyzed by the gas chromatography. As a result, a degree of conversion of methacrolein was 53.7%, methacrylic acid selectivity was 95.90, and a yield of methacrylic acid was 51.5%.

Example 23

A support including 42.9 mol % of silicon, 37.0 mol % of aluminum, 10.9 mol % of nickel and 9.1 mol % of magnesium was obtained in the same manner as in (1) of Example 1 except that 4.4 kg of aluminum oxide was used instead of 1.5 kg of aluminum nitrate nonahydrate, 0.93 kg of nickel oxide was used instead of 0.24 kg of nickel nitrate hexahydrate, 0.42 kg of magnesium oxide was used instead of 0.98 kg of magnesium nitrate hexahydrate, and that the calcining temperature is changed from 600° C. to 800° C. The Ni(X)/Al composition ratio was 0.30 on a mole basis and the Ni(X)/Mg(B) composition ratio was 1.20 on a mole basis. The specific surface area measured by the nitrogen adsorption method was 78 m$^2$/g, the pore volume was 0.27 mL/g and the average pore size was 5.2 nm. The bulk density was 1.02 CBD and the abrasion resistance was 0.1% by mass. The average particle size was found to be 62 µm on the basis of a result of the laser scattering particle size distribution measurement. Furthermore, the support was found to be free from break or crack and be in a substantially spherical shape on the basis of observation with a scanning electron microscope (SEM). As for the form of the solid material, an amorphous pattern similar to that of a silica gel was obtained as a result of the powder X-ray diffraction (XRD).

To 1 L of distilled water contained in a glass vessel, 300 g of the silica-based material obtained as above was added, and a prescribed amount of a dilute hydrochloric acid solution of a chloroauric acid aqueous solution and nickel nitrate hexahydrate was rapidly added dropwise thereto with stirring at 60° C. Subsequently, a 0.5 N sodium hydroxide aqueous solution was further added thereto for adjusting the aqueous solution to pH 8 and the mixed liquid was successively stirred for further 1 hour. Thereafter, hydrazine in an amount 1.2 times as large as a stoichiometric amount was added to the content of the glass vessel for reduction. A supernatant was removed by decantation from the content resulting from the reduction for collecting a precipitate, the precipitate was washed with distilled water until no Cl ions were detected and the washed substance was dried in a vacuum at 60° C., whereby obtaining a noble metal-supported material supporting 3.0% by mass of Au and 3.0% by mass of Ni (an AuNi/Si—Al—Ni—Mg composite oxide).

As for the noble metal-supported material, the specific surface area measured by the nitrogen adsorption method was 105 m$^2$/g, the pore volume was 0.27 mL/g and the average pore size was 4.0 nm. The average particle size was found to be 62 μm on the basis of a result of the laser scattering particle size distribution measurement. Furthermore, the noble metal-supported material was found to be free from break or crack and be in a substantially spherical shape on the basis of observation with a scanning electron microscope (SEM).

The fine structure of the noble metal-supported material was observed with a transmission electron microscope (TEM), resulting in finding that metal particles having a particle size of 4 to 5 nm were uniformly supported on the surface of the support. The metal particles had a number average particle size of 4.5 nm (calculated based on 100 particles).

Next, for evaluating the chemical stability of the noble metal-supported material obtained as described above, the pH swing test was performed in the same manner as in Example 1. As a result, after the pH swing process, the noble metal-supported material had a specific surface area of 107 m$^2$/g, a pore volume of 0.27 mL/g and an average pore size of 4.1 nm, which reveals that the structure had not been changed through the pH swing process. Furthermore, the average particle size of the metal particles obtained with a transmission electron microscope (TEM) was 4.7 nm (calculated based on 100 particles) and particle growth of the metal particles was minimally observed.

Methacrylic acid was produced from methacrolein by using the noble metal-supported material (the AuNi/Si—Al—Ni—Mg composite oxide) in the same manner as in Example 18. As a result, a degree of conversion of methacrolein was 38.9%, methacrylic acid selectivity was 94.9% and a yield of methacrylic acid was 36.7%.

Example 24

To 1 L of distilled water contained in a glass vessel, 300 g of the support obtained in Example 2 was added, and a prescribed amount of a diluent hydrochloric acid of a chloroauric acid aqueous solution and chloroplatinic acid was rapidly added dropwise thereto with stirring at 60° C. Subsequently, a 0.5 N sodium hydroxide aqueous solution was further added thereto for adjusting the aqueous solution to pH 8 and the mixed liquid was successively stirred for further 1 hour. Thereafter, hydrazine in an amount 1.2 times as large as a stoichiometric amount was added to the content of the glass vessel for reduction. A supernatant was removed by decantation from the content resulting from the reduction for collecting a precipitate, the precipitate was washed with distilled water until no Cl ions were detected and the washed substance was dried in a vacuum at 60° C., whereby obtaining a noble metal-supported material supporting 2.0% by mass of Au and 2.0% by mass of Pt (an AuPt/Si—Al—Zn—K composite oxide).

As for the noble metal-supported material, the specific surface area measured by the nitrogen adsorption method was 220 m$^2$/g, the pore volume was 0.27 mL/g and the average pore size was 3.9 nm. The average particle size was found to be 62 μm on the basis of a result of the laser scattering particle size distribution measurement. Furthermore, the noble metal-supported material was found to be free from break or crack and be in a substantially spherical shape on the basis of observation with a scanning electron microscope (SEM).

The fine structure of the noble metal-supported material was observed with a transmission electron microscope (TEM), resulting in finding that metal particles having a particle size of 3 to 4 nm were uniformly supported on the surface of the support. The metal particles had a number average particle size of 3.5 nm (calculated based on 100 particles).

Next, for evaluating the chemical stability of the noble metal-supported material obtained as described above, the pH swing test was performed in the same manner as in Example 1. As a result, after the pH swing process, the noble metal-supported material had a specific surface area of 217 m$^2$/g, a pore volume of 0.27 mL/g and an average pore size of 4.0 nm, which reveals that the structure had not been changed through the pH swing process. Furthermore, the average particle size of the metal particles obtained with a transmission electron microscope (TEM) was 3.7 nm (calculated based on 100 particles) and particle growth of the metal particles was minimally observed.

Methacrylic acid was produced from methacrolein by using the noble metal-supported material (the AuPt/Si—Al—Zn—K composite oxide) in the same manner as in Example 18. As a result, a degree of conversion of methacrolein was 63.1%, methacrylic acid selectivity was 96.3% and a yield of methacrylic acid was 60.8%.

Example 25

Methacrylic acid was produced from methacrolein by using the same noble metal-supported material (the Pd/Si—Al—Ni—Mg composite oxide) as that of Example 12 in the same manner as in Example 18. As a result, a degree of conversion of methacrolein was 6.0%, methacrylic acid selectivity was 66.6% and a yield of methacrylic acid was 4.0%.

Example 26

A stainless steel stirring reactor having a liquid phase part of 0.5 liter was charged with 10 g of the same noble metal-supported material (the Pd/Si—Al—Ni—Mg composite oxide) as that of Example 12 used as a catalyst and 10% by mass of an ethylene glycol aqueous solution. While stirring the content at a tip speed of stirring blade of the reactor of 1.5 m/sec, an oxidation reaction of ethylene glycol was carried out. The reaction temperature was set to 50° C. and the air was blown in at a rate of 350 ml/min at normal-pressure, and while supplying 2.5% by mass of an NaOH aqueous solution to the reactor so as to adjust the pH of the reaction system to 8 to 10, the reaction was carried out for 4 hours, and therefore, the catalyst was filtered out, and the thus obtained filtrate was evaporated to dryness with a rotary evaporator, so as to give 63 g of a white powder of sodium hydroxyacetate.

Example 27

A stirring reactor (500 ml) made of stainless steel was charged with 1 g of the same noble metal-supported material (the Pd/Si—Al—Ni—Mg composite oxide) as that of Example 12 used as a catalyst and 150 g of liquid phenol. After an atmosphere in a system was replaced with a nitrogen gas, a hydrogen gas was introduced into a gas phase part, whereby increasing the total pressure within the system up to 2.5 MPa. With the reaction temperature set to 140° C. and with stirring the content at a tip speed of stirring blade of 1.5 m/sec, a hydrogenation reaction of phenol into cyclohexanone was carried out. The resultant was cooled after conducting the reaction for 1 hour, a residual pressure was removed and the autoclave was opened, the catalyst was filtered out, and the thus obtained filtrate was analyzed by the gas chromatography. As a result, a degree of conversion to phenol was 99.7% and cyclohexanone selectivity was 91.3%.

Example 28

To 100 mL of distilled water contained in a glass vessel, 30 g of the silica-based material obtained in Example 4 was added, and prescribed amounts of a ruthenium chloride aqueous solution and a zinc nitrate aqueous solution were added dropwise thereto with stirring at 80° C., and furthermore, a 0.5 N sodium hydroxide aqueous solution was further added thereto for adjusting the aqueous solution to pH 8. After the mixed liquid was successively stirred for further 1 hour, the resultant mixed liquid was allowed to stand still for removing a supernatant, the thus obtained precipitate was washed with distilled water until no Cl ions were detected and the thus obtained solid material was dried at 105° C. for 16 hours and then calcined in the air at 300° C. for 3 hours. Subsequently, the resultant solid material was subjected to a reduction treatment at 350° C. for 3 hours in a hydrogen atmosphere, whereby obtaining a noble metal-supported material supporting 10.4% by mass of ruthenium and zinc in an atomic ratio of zinc/ruthenium of 0.11 (a RuZn/Si—Al—Fe—La composite oxide).

A Hastelloy autoclave of 1 liter was charged with 0.5 g of the noble metal-supported material (the RuZn/Si—Al—Fe—La composite oxide) and 280 mL of a 10% by mass zinc nitrate aqueous solution, an atmosphere in the autoclave was replaced with hydrogen while stirring, the temperature was increased to 150° C. and kept for 22 hours, whereby performing a pretreatment for a catalyst slurry. Thereafter, 140 mL of benzene was injected, and a partial hydrogenation reaction of benzene was carried out at a total pressure of 5 MPa with rapidly stirring. The thus obtained reaction solution was extracted over time, and a composition of the liquid phase was analyzed by the gas chromatography, resulting in finding that cyclohexene selectivity at a degree of conversion of benzene of 50% was 81.5%.

Example 29

To 100 mL of distilled water contained in a glass vessel, 30 g of the silica-based material obtained in Example 1 was added, a prescribed amount of a dilute hydrochloride solution of ruthenium chloride, chloroplatinic acid and tin chloride was added dropwise thereto with stirring at 80° C., and furthermore, a 0.5 N sodium hydroxide aqueous solution was further added thereto for adjusting the aqueous solution to pH 8. After the mixed liquid was successively stirred for further 1 hour, the resultant mixed liquid was allowed to stand still for removing a supernatant, the thus obtained precipitate was washed with distilled water until no Cl ions were detected and the thus obtained solid material was dried at 105° C. for 16 hours and then calcined in the air at 300° C. for 3 hours. Subsequently, the resultant solid material was subjected to a reduction treatment at 350° C. for 3 hours in a hydrogen atmosphere, whereby obtaining a noble metal-supported material supporting 6.1% by mass of ruthenium, 5.0% by mass of tin and 3.4% by mass of platinum (a RuSnPt/Si—Al—Ni—Mg composite oxide).

An autoclave of 30 mL was charged with 0.15 g of the noble metal-supported material (the RuSnPt/Si—Al—Ni—Mg composite oxide), 5 g of water, and 2.1 g of a mixture of succinic acid, glutaric acid and adipic acid including 23% by mass of succinic acid, 60% by mass of glutaric acid and 17% by mass of adipic acid, and an atmosphere in the autoclave was replaced with nitrogen at room temperature, and therefore, a hydrogen gas was introduced into a gas phase part for increasing the total pressure within the system to 2.0 MPa and the temperature was increased to 180° C. When the temperature reached 180° C., a hydrogen gas was introduced to increase the total pressure within the system to 15 MPa, and then, a hydrogenation reduction reaction was carried out for 10 hours. After completing the reaction, the catalyst was separated by decantation, and the catalyst was washed with ion-exchanged water. A mixture of the reaction solution separated by the decantation and the liquid used for washing the catalyst was analyzed by liquid chromatography and the gas chromatography for degrees of conversion of respective dicarboxylic acids and yields of diols, resulting in finding that degrees of conversion of succinic acid, glutaric acid and adipic acid were respectively 93%, 93% and 95%, and that yields of 1,4-butanediol, 1,5-pentanediol and 1,6-hexanediol were respectively 51%, 75% and 61%.

Industrial Applicability

The present invention may provide a silica-based material that has high mechanical strength and a high specific surface area and is excellent in resistance to acids and bases, and a noble metal-supported material including the silica-based material.

The invention claimed is:

1. A silica-based material comprising:

silicon;

aluminum;

at least one fourth period element selected from the group consisting of iron, cobalt, nickel and zinc; and at least one basic element selected from the group consisting of alkali metal elements, alkali earth metal elements and rare earth elements, wherein the silica-based material comprises 42 to 90 mol % of the silicon, 3 to 38 mol % of the aluminum, 0.5 to 20 mol % of the fourth period element and 2 to 38 mol % of the basic element, based on a total mole of the silicon, the aluminum, the fourth period element and the basic element, and the fourth period element is present in substantially the same concentration in the silica-based material.

2. The silica-based material according to claim 1, wherein a composition ratio of the fourth period element to the aluminum is 0.02 to 2.0 on a mole basis.

3. The silica-based material according to claim 1 or 2, wherein a composition ratio of the fourth period element to the basic element is 0.02 to 2.0 on a mole basis.

4. The silica-based material according to claim 1 or 2, wherein the fourth period element is nickel, the basic element is magnesium, and the silica-based material comprises 42 to 90 mol % of the silicon, 3 to 38 mol % of the aluminum, 0.5 to 20 mol % of the nickel and 2 to 38 mol % of the magnesium, based on a total mole of the silicon, the aluminum, the nickel and the magnesium.

5. The silica-based material according to claim 1, wherein the fourth period element is present in substantially the same concentration in the silica-based material such that a distribution range of the concentration is within 10% in a cross-section of the silica-based material observed by electron probe microanalysis (EPMA).

* * * * *